US010640529B2

(12) United States Patent
Coleman et al.

(10) Patent No.: US 10,640,529 B2
(45) Date of Patent: *May 5, 2020

(54) MULTISIGNAL LABELING REAGENTS AND PROCESSES AND USES THEREFOR

(71) Applicant: Enzo Life Science, Inc., Farmingdale, NY (US)

(72) Inventors: Jack Coleman, East Northport, NY (US); Elazar Rabbani, New York, NY (US); Jannis Stavrianopoulos, Bay Shore, NY (US); Praveen Pande, Holbrook, NY (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 231 days.

This patent is subject to a terminal disclaimer.

(21) Appl. No.: 15/849,997

(22) Filed: Dec. 21, 2017

(65) Prior Publication Data

US 2018/0127455 A1    May 10, 2018

Related U.S. Application Data

(60) Continuation of application No. 14/844,468, filed on Sep. 3, 2015, now Pat. No. 9,884,889, which is a division of application No. 13/065,101, filed on Mar. 14, 2011, now Pat. No. 9,156,986, which is a continuation-in-part of application No. 12/399,393, filed on Mar. 6, 2009, now Pat. No. 8,394,949, which is a division of application No. 10/407,818, filed on Apr. 3, 2003, now Pat. No. 7,514,551.

(51) Int. Cl.
| | |
|---|---|
| *C07H 21/00* | (2006.01) |
| *C12Q 1/68* | (2018.01) |
| *C07D 219/08* | (2006.01) |
| *C07D 491/22* | (2006.01) |
| *C07H 21/04* | (2006.01) |
| *C09B 11/08* | (2006.01) |
| *C12Q 1/6818* | (2018.01) |
| *C07D 405/14* | (2006.01) |
| *C09B 11/00* | (2006.01) |
| *C09B 57/02* | (2006.01) |
| *C09B 11/24* | (2006.01) |
| *G01N 33/533* | (2006.01) |
| *G01N 33/58* | (2006.01) |

(52) U.S. Cl.
CPC ............ *C07H 21/00* (2013.01); *C07D 219/08* (2013.01); *C07D 405/14* (2013.01); *C07D 491/22* (2013.01); *C07H 21/04* (2013.01); *C09B 11/00* (2013.01); *C09B 11/08* (2013.01); *C09B 11/24* (2013.01); *C09B 57/02* (2013.01); *C12Q 1/68* (2013.01); *C12Q 1/6818* (2013.01); *G01N 33/533* (2013.01); *G01N 33/582* (2013.01)

(58) Field of Classification Search
CPC ..... C12Q 1/6806; C12Q 1/6818; C07H 21/00

USPC ........................................... 536/26.6; 435/6.1
See application file for complete search history.

(56) References Cited

U.S. PATENT DOCUMENTS

| | | | |
|---|---|---|---|
| 4,081,525 | A | 3/1978 | Knight et al. |
| 4,257,774 | A | 3/1981 | Richardson et al. |
| 4,547,569 | A | 10/1985 | Letsinger et al. |
| 4,585,862 | A | 4/1986 | Wang et al. |
| 4,692,509 | A | 9/1987 | Dattagupta et al. |
| 4,711,955 | A | 12/1987 | Ward et al. |
| 4,876,187 | A | 10/1989 | Duck et al. |
| 4,948,882 | A | 8/1990 | Ruth et al. |
| 4,952,685 | A | 8/1990 | Stavrianopoulos et al. |
| 4,996,143 | A | 2/1991 | Heller et al. |
| 5,013,831 | A | 5/1991 | Stavrianopoulos et al. |
| 5,175,270 | A | 12/1992 | Nilsen et al. |
| 5,241,060 | A | 8/1993 | Engelhardt et al. |
| 5,446,137 | A | 8/1995 | Maag |
| 5,696,251 | A | 12/1997 | Arnold et al. |
| 5,945,526 | A | 8/1999 | Lee et al. |
| 6,008,373 | A | 12/1999 | Waggoner et al. |
| 6,046,038 | A | 4/2000 | Nilsen et al. |
| 7,166,478 | B2 | 1/2007 | Stavrianopoulos et al. |
| 7,514,551 | B2 | 4/2009 | Rabbani et al. |
| 8,048,659 | B1 | 11/2011 | Leif |
| 8,394,949 | B2 | 3/2013 | Rabbani et al. |
| 2003/0175828 | A1 | 9/2003 | Lazar |
| 2004/0161741 | A1 | 8/2004 | Rabbani et al. |
| 2005/0137388 | A1 | 6/2005 | Rabbani et al. |
| 2005/0181383 | A1 | 8/2005 | Su |
| 2006/0024738 | A1 | 2/2006 | Rabbani et al. |
| 2010/0273145 | A1 | 10/2010 | Pergolizzi et al. |
| 2011/0318788 | A1 | 12/2011 | Coleman et al. |
| 2012/0115169 | A1 | 5/2012 | Mullenix et al. |

FOREIGN PATENT DOCUMENTS

| | | |
|---|---|---|
| EP | 0450594 | 10/1991 |
| EP | 0128332 | 8/1995 |
| EP | 1275737 | 1/2004 |
| EP | 1344895 | 3/2004 |
| WO | WO 2000/029624 | 5/2000 |
| WO | WO 2001/072766 | 10/2001 |

OTHER PUBLICATIONS

Blomberg et al., Terbium and Rhodamine as Labels in a Homogeneous Time-resolved Fluorometic Energy Transfer Assay of the beta Subunit of Human Chorionic Gonadotropin in Serum, Clinical Chemistry 1999, 855-861, 45(6).

(Continued)

*Primary Examiner* — Jezia Riley
(74) *Attorney, Agent, or Firm* — Paul Diamond, Esq.

(57) ABSTRACT

Provided are compounds comprising two DNA supramolecular binding molecules covalently joined by a linker group. Also provided are multisignal labeling reagents comprising (i) an oligomer of nucleotides or nucleotide analogs; (ii) a DNA supramolecular binding molecule noncovalently bound to the oligomer; and (iii) a first reactive group or a first partner of a first binding pair covalently bound to the oligomer. Additionally provided are methods of producing multisignal labeling reagents.

24 Claims, 3 Drawing Sheets

Specification includes a Sequence Listing.

(56) References Cited

OTHER PUBLICATIONS

Cayman Chemical Company, Cyclic AMP EIA Kit, http://www.caymanchem.com/pdfs/581001.pdf.
Chabardes et al., Adenylate Cyclase Responsiveness to Hormones in Various Portions of the Human Nephron, J. Clin. Invest. 1980, 439-448, 65.
Charlton and Porter, Isolation of Anti-Hapten Specific Antibody Fragments from Combinatorial Libraries, Methods in Molecular Biology 2002, 159-171, 178.
Enzo Life Sciences, Inc., cAMP Complete ELISA kit, http://static.enzolifesciences.com/fileadmin/files/manual/ADI-900-163_insert.pdf.
Glover et al., Hairpin-Shaped Heterometallic Luminescent Lanthanide Complexes for DNA Intercalative Recognition, J. Am. Chem. Soc. 2003, 9918-9919, 125.
Grill and Cerasi, Stimulation by D-Glucose of Cyclic Adenosine 3': 5'-Monophosphate Accumulation and Insulin Release in Isolated Pancreatic Islets of the Rat, The Journal of Biological Chemistry 1974, 4196-4201, 249(13).
Haynes, Jr., Robert C., The Activation of Adrenal Phosphorylase by the Adrenocorticotropic Hormone, The Journal of Biological Chemistry 1958, 1220-1222, 233.
Lee et al., DNA sequencing with dye-labeled terminators and T7 DNA polymerase: effect of dyes and dNTPs on incorporation of dye-terminators and probability analysis of termination fragments, Nucleic Acids Research, 1992, 2471-2483, 20(10).
Lipkin et al., Adenosine 3' : 5'-phosphoric Acid : A Proof of Structure, Journal of the American Chemical Society 1959, 6198-6203, 81.
Mayilo et al., Competative homogeneous digoxigenin immunoassay based on fluorescence quenching by gold nanoparticles, Analytica Chimica Acta 2009,119-122, 646.
O'Beirne and Cooper, Heterogeneous enzyme immunoassay, The Journal of Histochemistry and Cytochemistry 1979, 1148-1162, 27(8).
Perkin Elmer, AlphaScreen CAMP Assay Kit, http://www.perkinelmer.com/Catalog/Product/ID/6760625D.
Promega, GloSensor CAMP Assay, http://www.promega.com/products/drug-discovery/gpcr-assays/glosensor-camp-assay/.
Szentivanyi, Andor, The beta adrenergic theory of the atopic abnormality in bronchial asthma, Journal of Allergy 1968, 203-232, 42.
Wang et al., Development of a Cyclic Adenosine Monophosphate Assay for Gi-Coupled G Protein-Coupled Receptors by Ultilizng the Endogenous Calcitonin Activity in Chinese Hampster Ovary Cells, Assay and Drug Development Technologies 2011, 522-531, 9.
Winter et al., Making antibodies by phage display technology, Annu. Rev. Immonol. 1994, 433-455, 12.
Wong et al., Reproducibility and Correlations of Multiplex Cytokine Levels in Asymptomatic Persons, Cancer Epidemiol Biomarkers Prev 2008, 3450-3456, 17(12).
Halloran and Parker, "The preparation of nucleotide-protein conjugates: carbodimides as coupling agents," J. Immunol., vol. 96, p. 373 (1966).
Kessler et al., "Methods for Nonradioactive Labeling of Nucleic Acids," Nonisotopic Probing, Blotting and Sequencing, 2nd edition, Larry J. Kricka (Ed.), Academic Press, Inc., San Diego, CA. pp. 42-109 (1995).
Lee et al., "DNA sequencing with dye-labeled terminators and T7 DNA polymerase: effect of dyes and dNTPs on incorporation of dye-terminators and probability analysis of termination fragments," Nucl. Acids Res., vol. 20, pp. 2471-2488 (1992).
Loeschner and Engels, "The applications of universal DNA base analogues," Nucleosides Nucleotides, vol. 7, pp. 729 (1988).
Nielsen et al., "Sequence-selective recognition of DNA by strand displacement with a thymine-substituted polyamide," Sciences, vol. 254, p. 1497 (1991).
Jablonski et al., "Preparation of oligodeoxynucleotide-alkaline phosphatase conjugates and their uses as hybridization probes." Nucl. Acids. Res., vol. 14, pp. 6115-6128 (1986).
Ono et al., "2'-Fluoro modified nucleic acids: polymerase-directed synthesis, properties and stability to analysis by matrix-assisted laser desorption/ionization mass spectrometry," Nucleic Acids Research, vol. 25, No. 22, pp. 4581-4588 (1997).
Stec et al., "Automated solid-phase synthesis, separation, and stereochemistry of phosphorothioate analogs of oligodeoxyribonucleotides," J. Am. Chem. Soc., vol. 106, pp. 6077-6079 (1984).
Schwarz et al., Nature, vol. 314, pp. 111-114 (1995).
Walling et al., "quantum dots for Live Cell and In vivo Imaging," Int. J. Mol. Sci., vol. 10, pp. 441-491 (2009).
Asseline et al., Oligodeoxynucleotides covalently linked to intercalating dyes as base sequence-specific ligands. influence of dye attachment site, EMBO , 1984, 795-800, 3.
Canellakis et al., Diacridines-double intercalators as chemotherapeutic agents, Biochemical Pharmacology, 1976, 231-236, 25.
Canellakis et al., Diacridines:bifunctional intercalators I. chemistry, physical chemistry and growth inhibitory properties, Biochimica et Biophysica Acta,1976, 277-289, 418.
Canellakis et al., Diacridines:bifunctional intercalators II. The biological effects of putrescine, spermidine and spermine diacridines on HeLa cells and on the L-1210 and P-388 leukemia cells, Biochimica et Biophysics Acta, 1976, 290-299, 418.
Canellakis et al., Diacridines:bifunctional intercalators III. definition of the general site of action, Biochimica et Biophysica Acta, 1976, 300-314, 418.
Capelle et al., Deoxyribonucleic acid bifunctional intercalators: kinetic investigation of the binding of several acridine dimers to deoxyribonucleic acid, Biochemistry, 1979, 3354-3362, 18.
Chen et al., Diacridines, bifunctional intercalators. chemistry and antitumor activity, Journal of Medicinal Chemistry, 1978, 868-874, 21.
Christy et al., DNA binding site of the growth factor-inducible protein Zif268, PNAS, 1989, 8737-8741, 86.
Elling et al., Conversion of antagonist-binding site to metal ion site in the tachykinin NK-1 receptor, Nature, 1995, 74-77, 374.
Fico et al., Bifunctional intercalators: relationship of antitumor activity of disacridines to the cell membrane; Science, 1977, 53-56, 198.
Gaugain et al., DNA bifunctional intercalators. 1. Synthesis and conformational properties of an ethidium homodimer and of an acridine ethidium heterdimer, Biochemistry, 1978, 5071-5077, 17.
Gaugain et al., DNA bifunctional intercalators. 2. Florescence properties and Dna binding interaction of an ethidium homodimer and an acridine ethidium heterodimer, Biochemistry, 1978, 5078-5088, 17.
Genest et al., Investigation of DNA dynamics and drug-DNA interaction by steady state fluorescence anistropy, Nucleic Acids Res., 1985, 2603-2615, 13.
Georghiou, S., Interaction of acridine drugs with DNA and nucleotides, Photochemistry and Photobiology, 1977, 59-68, 26.
Hampshire, A. and Fox, K., Preferred binding sites for the bifunctional intercalator TANDEM determined using DNA fragments that contain every symmetrical hexanucleotide sequence, Analytical Biochemistry, 2008, 298-303, 374.
Hannon, M., Supramolcular DNA recognition, Chemical Society Reviews, 2007, 280-295, 36.
King et al., Interactions of some novel amide-linked Bis(acridines) with deoxyribonucleic acid, Biochemistry, 1982, 4982-4989, 21.
Kobuta, Y. and Steiner, R., Fluorescence decay and quantum yield characteristics of acridine orange and proflavine bound to DNA, Biophysical Chemistry, 1977, 279-289, 6.
Loakes, D., The applications of universal DNA base analogues, Nucleic acids Res. 2001, 2437-2447, 29.
Mincheva et al., Chromosomal integration sites of human papillomavirus dna in three cervical cancer cell lines mapped by in situ hybridization, Med Microbiol Immunol.,1987, 245-256, 176.
Moloney et al., Synthesis of acridine-based DNA bis-intercalating agents, Molecules, 2001, 230-243, 6.

(56) References Cited

OTHER PUBLICATIONS

Timtcheva et al., Homodimeric monomethine cyanine dyes as fluorescent probes of biopolymers, J. Photochemistry and Photobiology B: Biology, 2000, 130-135, 58.
Wakelin et al., Structural limitations on the bifunctional intercalation of diacridines into DNA, Biochemistry, 1978, 5057-5063, 17.
Wright et al., Effects of ring substituents and linker chains on the bifunctional intercalation of diacridines into deoxyribonucleic acid, Biochemistry, 1980, 5825-5836, 19.

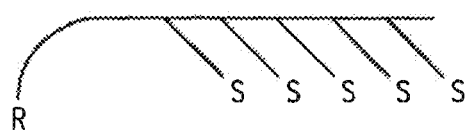
(a) polymer with Reactive group "R" and signal groups "S"

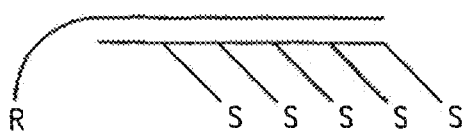
(b) polymer with Reactive group "R" bound to second polymer with signal groups "S"

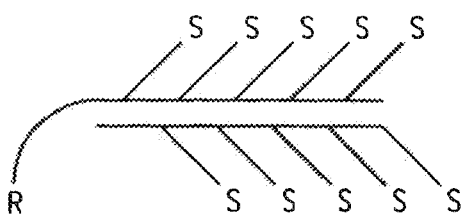
(c) polymer with Reactive group "R" and signal groups S bound to second polymer with signal groups "S"

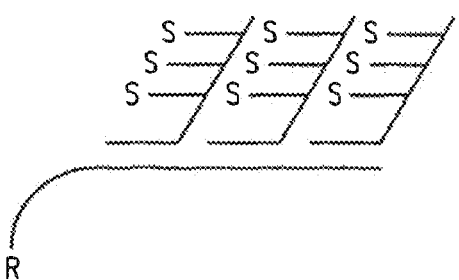
(d) polymer with Reactive group "R" bound to multiple polymers with signal groups "S"

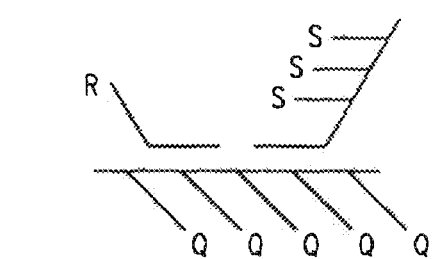
(e) polymer with charged groups "Q" bound to polymer with Reactive group "R" and polymer with signal groups "S"

Examples of arrangements of R, S and Q in polymers

FIG. 1

HeLa (30-50 copies)
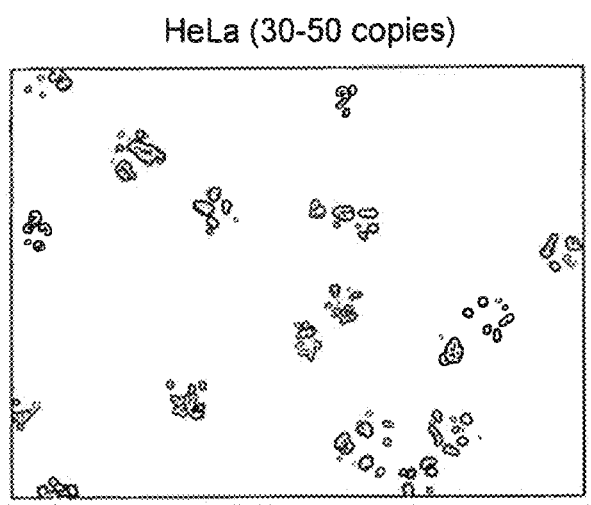
SiHa (1-5 copies)
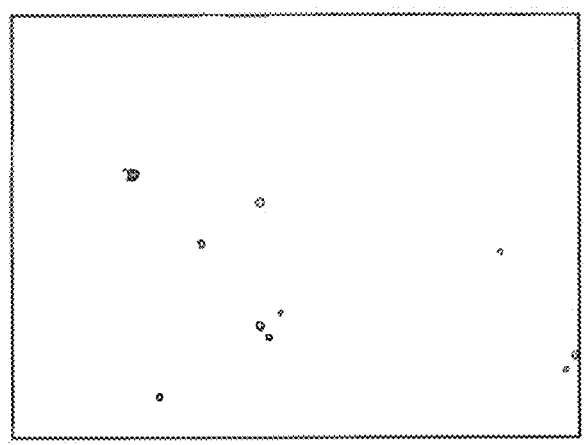
SK-N-SH (0 copies)
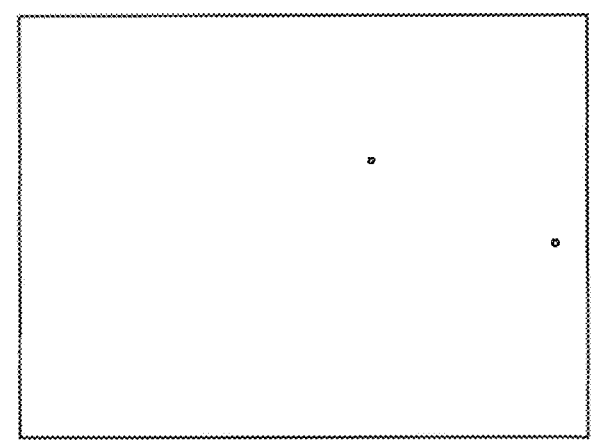
FIG. 3

SEQUENCE LISTING

```
<160> NUMBER OF SEQ ID NOS: 24

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-phosphate group
<220> FEATURE:
<221> NAME/KEY: modified_base
<222> LOCATION: (3)..(3)
<223> OTHER INFORMATION: Allylamine modified uridine moiety
<220> FEATURE:
<221> NAME/KEY: modified_base
<222> LOCATION: (9)..(9)
<223> OTHER INFORMATION: Allylamine modified uridine moiety
<220> FEATURE:
<221> NAME/KEY: modified_base
<222> LOCATION: (15)..(15)
<223> OTHER INFORMATION: Allylamine modified uridine moiety
<220> FEATURE:
<221> NAME/KEY: modified_base
<222> LOCATION: (21)..(21)
<223> OTHER INFORMATION: Allylamine modified uridine moiety
<220> FEATURE:
<221> NAME/KEY: modified_base
<222> LOCATION: (27)..(27)
<223> OTHER INFORMATION: Allylamine modified uridine moiety
<220> FEATURE:
<221> NAME/KEY: modified_base
<222> LOCATION: (33)..(33)
<223> OTHER INFORMATION: Allylamine modified uridine moiety

<400> SEQUENCE: 1
ttutttttut ttttuttttt utttttuttt ttu                              33

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Uridine with a fluorescein label
<220> FEATURE:
```

```
<221> NAME/KEY: modified_base
<222> LOCATION: (8)..(8)
<223> OTHER INFORMATION: Uridine with a fluorescein label
<220> FEATURE:
<221> NAME/KEY: modified_base
<222> LOCATION: (15)..(15)
<223> OTHER INFORMATION: Uridine with a fluorescein label
<220> FEATURE:
<221> NAME/KEY: modified_base
<222> LOCATION: (22)..(22)
<223> OTHER INFORMATION: Uridine with a fluorescein label
<220> FEATURE:
<221> NAME/KEY: modified_base
<222> LOCATION: (29)..(29)
<223> OTHER INFORMATION: Uridine with a fluorescein label
<220> FEATURE:
<223> OTHER INFORMATION: 3'-amidated

<400> SEQUENCE: 2
uttttttutt ttttutttt tutttttu                                   29

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Allylamine modified uridine
<220> FEATURE:
<221> NAME/KEY: modified_base
<222> LOCATION: (7)..(7)
<223> OTHER INFORMATION: Allylamine modified uridine
<220> FEATURE:
<221> NAME/KEY: modified_base
<222> LOCATION: (13)..(13)
<223> OTHER INFORMATION: Allylamine modified uridine
<220> FEATURE:
<221> NAME/KEY: modified_base
<222> LOCATION: (19)..(19)
<223> OTHER INFORMATION: Allylamine modified uridine
<220> FEATURE:
<221> NAME/KEY: modified_base
<222> LOCATION: (25)..(25)
<223> OTHER INFORMATION: Allylamine modified uridine

<400> SEQUENCE: 3 uttttttuttt ttutttttut ttttutt                                   27

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 3'-amidated

<400> SEQUENCE: 4
uttttttutt ttttutttt tuttttttut ttttutttt ttutttttu ttttttt      57

<210> SEQ ID NO 5
<211> LENGTH: 12
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: Allylamine modified uridine
<220> FEATURE:
<221> NAME/KEY: modified_base
<222> LOCATION: (8)..(8)
<223> OTHER INFORMATION: Allylamine modified uridine
<220> FEATURE:
<221> NAME/KEY: modified_base
<222> LOCATION: (12)..(12)
<223> OTHER INFORMATION: Allylamine modified uridine

<400> SEQUENCE: 5
gtgugtgugt gu                                                          12

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (51)..(51)
<223> OTHER INFORMATION: Biotin dU; may or may not be present and if not
      present 3' is amidated

<400> SEQUENCE: 6
acacacacac acacacacac acacacacac acacacacac acacacacac u              51

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: Allylamine modified uridine
<220> FEATURE:
<221> NAME/KEY: modified_base
<222> LOCATION: (13)..(13)
<223> OTHER INFORMATION: Allylamine modified uridine

<400> SEQUENCE: 7
tgcugctgcu gcugc                                                       15

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: 3'-amidated

<400> SEQUENCE: 8
gcagcagcag cagcagcagc agcagcagca gcagcagcag cagcagcagc agcagcagca    60
gca                                                                  63

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: Allylamine modified uridine
<220> FEATURE:
<221> NAME/KEY: modified_base
<222> LOCATION: (13)..(13)
<223> OTHER INFORMATION: Allylamine modified uridine

<400> SEQUENCE: 9
tcgucgtcgu cgucg                                                     15

<210> SEQ ID NO 10
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-amidated

<400> SEQUENCE: 10
cgacgacgac gacgacgacg acgacgacga cgacgacgac gacgacgacg acgacgacga    60
cga                                                                  63

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: Allylamine modified uridine
<220> FEATURE:
<221> NAME/KEY: modified_base
<222> LOCATION: (8)..(8)
<223> OTHER INFORMATION: Allylamine modified uridine
<220> FEATURE:
<221> NAME/KEY: modified_base
<222> LOCATION: (12)..(12)
<223> OTHER INFORMATION: Allylamine modified uridine
<220> FEATURE:
<221> NAME/KEY: modified_base
<222> LOCATION: (16)..(16)
<223> OTHER INFORMATION: Allylamine modified uridine
<220> FEATURE:
<221> NAME/KEY: modified_base
<222> LOCATION: (20)..(20)

```
<223> OTHER INFORMATION: Allylamine modified uridine
<220> FEATURE:
<221> NAME/KEY: modified_base
<222> LOCATION: (24)..(24)
<223> OTHER INFORMATION: Allylamine modified uridine
<220> FEATURE:
<221> NAME/KEY: modified_base
<222> LOCATION: (28)..(28)
<223> OTHER INFORMATION: Allylamine modified uridine
<220> FEATURE:
<221> NAME/KEY: modified_base
<222> LOCATION: (32)..(32)
<223> OTHER INFORMATION: Allylamine modified uridine

<400> SEQUENCE: 11
gtgugtgugt gugtgutttu tttutttutt tu                               32

<210> SEQ ID NO 12
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Biotin U
<220> FEATURE:
<221> NAME/KEY: modified_base
<222> LOCATION: (2)..(2)
<223> OTHER INFORMATION: Allylamine modified uridine moiety
<220> FEATURE:
<221> NAME/KEY: modified_base
<222> LOCATION: (14)..(14)
<223> OTHER INFORMATION: Allylamine modified uridine moiety
<220> FEATURE:
<221> NAME/KEY: modified_base
<222> LOCATION: (26)..(26)
<223> OTHER INFORMATION: Allylamine modified uridine moiety
<220> FEATURE:
<221> NAME/KEY: modified_base
<222> LOCATION: (38)..(38)
<223> OTHER INFORMATION: Allylamine modified uridine moiety
<220> FEATURE:
<221> NAME/KEY: modified_base
<222> LOCATION: (50)..(50)
<223> OTHER INFORMATION: Allylamine modified uridine moiety

<400> SEQUENCE: 12
uugtgtgtgt gtgugtgtgt gtgtgugtgt gtgtgtgugt gtgtgtgtgu gtgtgtgtgt   60
g                                                                  61

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgtgtgtgtg tgtgtgtgtg                                              20

<210> SEQ ID NO 14
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 14
acacacacac acacacacac                                              20

<210> SEQ ID NO 15
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Biotin U
<220> FEATURE:
<221> NAME/KEY: modified_base
<222> LOCATION: (2)..(2)
<223> OTHER INFORMATION: Fluorescein modified cytidine moiety
<220> FEATURE:
<221> NAME/KEY: modified_base
<222> LOCATION: (14)..(14)
<223> OTHER INFORMATION: Fluorescein modified cytidine moiety
<220> FEATURE:
<221> NAME/KEY: modified_base
<222> LOCATION: (26)..(26)
<223> OTHER INFORMATION: Fluorescein modified cytidine moiety
<220> FEATURE:
<221> NAME/KEY: modified_base
<222> LOCATION: (38)..(38)
<223> OTHER INFORMATION: Fluorescein modified cytidine moiety
<220> FEATURE:
<221> NAME/KEY: modified_base
<222> LOCATION: (50)..(50)
<223> OTHER INFORMATION: Fluorescein modified cytidine moiety

<400> SEQUENCE: 15
ucacacacac acacacacac acacacacac acacacacac acacacacac acacacacac    60
a                                                                    61

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: Allylamine modified uridine moiety
<220> FEATURE:
<221> NAME/KEY: modified_base
<222> LOCATION: (15)..(15)
<223> OTHER INFORMATION: Allylamine modified uridine moiety

<400> SEQUENCE: 16
tgtgugtgtg tgtgugtgtg                                              20

<210> SEQ ID NO 17
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: 5'-amino-C6

<400> SEQUENCE: 17
ttgctgaggt catggatcga ga                                            22

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-amino-C6

<400> SEQUENCE: 18
ttttgacacg ggtcctatgc cttgacacgg gtcctatgcc ttgacacggg tcctatgcct   60

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-amino-C6
<220> FEATURE:
<223> OTHER INFORMATION: 3' may or may not be biotinylated

<400> SEQUENCE: 19
ttttagcttt tcagttttga cta                                           23

<210> SEQ ID NO 20
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
acttctactt ctacttctac ttctacttct acttctactt ctacttctac tcttactctt   60
actcttcatt ggtcatctcg atccatgacc tcagc                              95

<210> SEQ ID NO 21
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tactgctact gctacttcta ctgctactgc tacttctact gctactctga ctctgactct   60
tcattggtca ctacaccaac agcatgac                                      88

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 22
aggcatagga cccgtgtctt t                                              21

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtcatgctgt tggtgtag                                                  18

<210> SEQ ID NO 24
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-biotin

<400> SEQUENCE: 24
tatgacacgg gtcctatgcc ttgacacggg tcctatgcct tgacacgggt cctatgcctt    60
gacacgggtc ctatgccttg acacgggtcc tatgcct                            97
```

MULTISIGNAL LABELING REAGENTS AND PROCESSES AND USES THEREFOR

CROSS-REFERENCE TO RELATED APPLICATIONS

This application is a continuation of U.S. Ser. No. 14/844,468, filed Sep. 3, 2015, which is a divisional of U.S. Ser. No. 13/065,101, filed Mar. 14, 2011, now U.S. Pat. No. 9,156,986, which is a continuation-in-part application of U.S. application Ser. No. 12/399,393, filed Mar. 6, 2009, now U.S. Pat. No. 8,394,949, which is a divisional of U.S. application Ser. No. 10/407,818, filed Apr. 3, 2003, now U.S. Pat. No. 7,514,551, each of which is hereby incorporated by reference in its entirety.

BACKGROUND OF THE INVENTION

(1) Field of the Invention

The present application generally relates to compositions useful as multisignal labeling reagents. More particularly, these reagents are useful in a number of biochemical applications, including attaching signals to analyte-specific moieties, such as proteins and more specifically, antibodies. These reagents are also useful in labeling samples contemplated to be assayed in protein array systems. The addition of multiple signals in such reagents is useful in increasing detection sensitivity.

(2) Description of the Related Art

The use of non-radioactive labels in biochemistry and molecular biology has grown exponentially in recent years. Among the various compounds used as non-radioactive labels, aromatic dyes that produce fluorescent or luminescent signal are especially useful. Notable examples of such compounds include fluorescein, rhodamine, coumarin and cyanine dyes such as Cy3 and Cy5. Composite dyes have also been synthesized by fusing two different dyes together (Lee et al., (1992) Nucl. Acids Res. 20:2471-2488; Lee et al., U.S. Pat. No. 5,945,526 and Waggoner et al., in U.S. Pat. No. 6,008,373, all of which are hereby incorporated by reference).

Non-radioactive labeling methods were initially developed to attach signal-generating groups onto proteins. This was achieved by modifying labels with chemical groups such that they would be capable of reacting with the amine, thiol, and hydroxyl groups that are naturally present on proteins. Examples of reactive groups that were used for this purpose included activated esters such as N-hydroxysuccinimide esters, isothiocyanates and other compounds. Consequently, when it became desirable to label nucleotides and nucleic acids by non-radioactive means, methods were developed to convert nucleotides and polynucleotides into a form that made them functionally similar to proteins. For instance, U.S. Pat. No. 4,711,955 (incorporated by reference) disclosed the addition of amines to the 8-position of a purine, the 5-position of a pyrimidine and the 7-position of a deazapurine. The same methods that could add a label to the amine group of a protein could now be applied towards these modified nucleotides.

Labeled nucleotides have been used for the synthesis of DNA and RNA probes in many enzymatic methods including terminal transferase labeling, nick translation, random priming, reverse transcription, RNA transcription and primer extension. Labeled phosphoramidite versions of these nucleotides have also been used with automated synthesizers to prepare labeled oligonucleotides. The resulting labeled probes are widely used in such standard procedures as northern blotting, Southern blotting, in situ hybridization, RNAse protection assays, DNA sequencing reactions, DNA and RNA microarray analysis and chromosome painting.

There is an extensive literature on chemical modification of nucleic acids by means of which a signal moiety is directly or indirectly attached to a nucleic acid. Primary concerns of this art have been with regard to which site in a nucleic acid is used for attachment i.e. sugar, base or phosphate analogs and whether these sites are disruptive or non-disruptive (see for instance the disclosures of U.S. Pat. Nos. 4,711,955 and 5,241,060; both patents incorporated by reference), the chemistry at the site of attachment that allows linkage to a reactive group or signaling moiety a spacer group usually consisting of a single aromatic group (U.S. Pat. Nos. 4,952,685 and 5,013,831, both hereby incorporated by reference) or a carbon/carbon aliphatic chain to provide distance between the nucleic acid and a reactive group or signaling moiety and a reactive group at the end of the spacer such as an OH, NH, SH or some other group that can allow coupling to a signaling moiety and the nature of the signaling moiety.

More recently, U.S. Pat. No. 7,166,478 (incorporated by reference) has disclosed novel labeling reagents that comprise a reactive group capable of creating a carbon-carbon bond between a marker or label and a desirable target molecule. This is in contrast to labeling reagents described previously, which employed protein derived chemistries involving formation of a bond between an amine, sulfhydryl or hydroxyl group and an appropriate reactive group. The presence and nature of the linker arm may also increase the biological or chemical activity of the labeled target molecule. Linker arms that may be used to provide appropriate spacing of signal groups in nucleic acids were also provided in this disclosure.

BRIEF SUMMARY OF THE INVENTION

In some embodiments, a compound comprising two DNA supramolecular binding molecules covalently joined by a linker group is provided. The compound further comprises a detectable label bound thereto, where the detectable label is not either of the two DNA supramolecular binding molecules.

In other embodiments, a multisignal labeling reagent is provided. The multisignal labeling reagent comprises (i) an oligomer of nucleotides or nucleotide analogs; (ii) a DNA supramolecular binding molecule noncovalently bound to the oligomer; and (iii) a first reactive group or a first partner of a first binding pair covalently bound to the oligomer.

Also provided herein is a method of producing a multisignal labeling reagent. The method comprises (a) obtaining (i) a primer comprising an oligonucleotide and a first reactive group or a first partner of a first binding pair at the 5' end of the oligonucleotide; (ii) a template comprising a nucleic acid comprising a first sequence that is complementary to the oligonucleotide and a second sequence that extends in the 5' direction from the first sequence; (iii) a polymerase capable of extending the oligonucleotide along the template nucleic acid when the template nucleic acid is hybridized to the oligonucleotide at the first sequence; and (iv) nucleotide triphosphates (NTPs) or analogs thereof that are capable of being incorporated into the extended oligonucleotide, wherein at least one of the NTPs or analogs comprises a non-radioactive detectable label, a second reactive group or a first partner of a second binding pair; and (b) combining the primer, template, polymerase and NTPs or analogs under conditions such that the oligonucleotide hybridizes to the first sequence and is extended along the second sequence, where the extended oligonucleotide comprises at least two NTPs or analogs incorporated therein that comprise a non-radioactive detectable label, a second reactive group or a first partner of a second binding pair. In these embodiments, (A) if at least one of the two or more NTPs or analogs incorporated into the extended oligonucleotide comprises a second reactive group, the method further comprises combining the extended oligonucleotide with a first compound comprising a non-radioactive detectable label covalently linked to a moiety capable of reacting with the second reactive group such that the label is covalently linked to the extended primer, and (B) if at least one of the two or more NTPs or analogs incorporated into the extended oligonucleotide comprises a first partner of the second binding pair, the method further comprises combining the extended primer with a second compound comprising the non-radioactive detectable label covalently linked to a second binding partner of the second binding pair.

Further provided is another method of producing a multisignal labeling reagent. This method comprises (a) obtaining (i) a primer comprising an oligonucleotide; (ii) a template comprising a nucleic acid comprising a first sequence that is complementary to the oligonucleotide and a second sequence that extends in the 5' direction from the first sequence; (iii) a polymerase capable of extending the oligonucleotide along the template nucleic acid when the template nucleic acid is hybridized to the oligonucleotide at the first sequence; (iv) nucleotide triphosphates (NTPs) or analogs thereof that are capable of being incorporated into the extended oligonucleotide, wherein at least one of the NTPs or analogs comprises a non-radioactive detectable label, a second reactive group or a first partner of a second binding pair; and (v) a polymer capable of binding to more than one of the extended oligonucleotide, wherein the polymer comprises a first reactive group or a first partner of a first binding pair; (b) combining the primer, template, polymerase and NTPs or analogs under conditions such that the oligonucleotide hybridizes to the first sequence and is extended along the second sequence, where the extended oligonucleotide comprises at least two NTPs or analogs incorporated therein that comprise a non-radioactive detectable label, a second reactive group or a first partner of a second binding pair; and (c) combining the extended oligonucleotide with the polymer under conditions such that at least two of the extended oligonucleotides bind to the polymer. In these embodiments, (A) if at least one of the two or more NTPs or analogs incorporated into the extended oligonucleotide comprises a second reactive group, the method further comprises combining the extended oligonucleotide with a first compound comprising a non-radioactive detectable label covalently linked to a moiety capable of reacting with the second reactive group such that the label is covalently linked to the extended primer, and (B) if at least one of the two or more NTPs or analogs incorporated into the extended oligonucleotide comprises a first partner of the second binding pair, the method further comprises combining the extended primer with a second compound comprising the non-radioactive detectable label covalently linked to a second binding partner of the second binding pair.

BRIEF DESCRIPTION OF THE DRAWINGS

FIG. 1 shows various arrangements of single-stranded and double-stranded nucleic acid multisignal labeling reagents.

FIG. 3 is fluorescent micrographs of HeLa cells, SiHa cells and SK-N-SH cells stained with a multisignal labeling reagent prepared by the invention extended primer method, where the multisignal labeling reagent was designed to detect HPV 16/18 DNA integrated into the chromosome of the cells, where the cells have the indicated number of copies of the HPV 16/18 DNA.

DETAILED DESCRIPTION OF THE INVENTION

Figure 2:
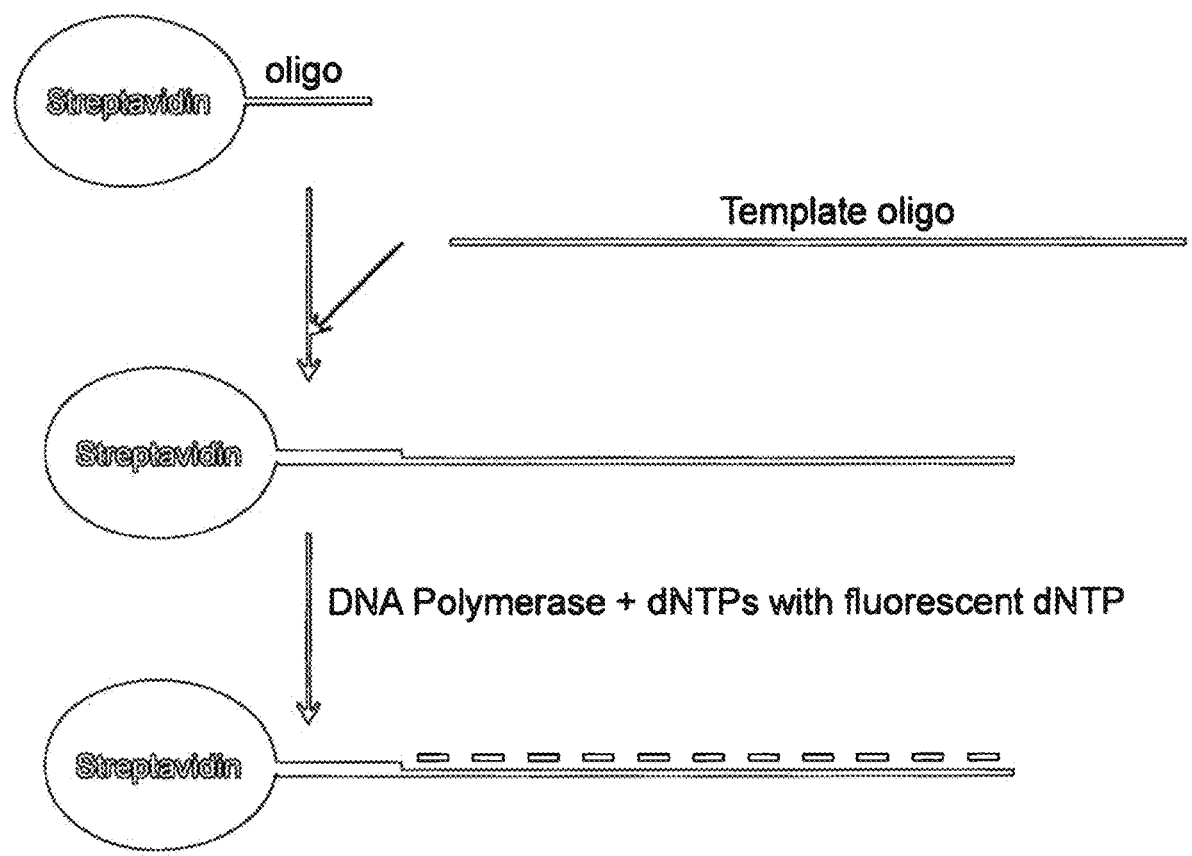
FIG. 2 is a diagram of an extended primer method of synthesizing a multisignal labeling reagent.

The present invention discloses methods and compositions for making labeled targets, labeled analytes and labeled analyte specific moieties that can have increased sensitivity and solubility compared to previous art. Examples of analyte specific moieties that may find use with the present invention can include but not be limited to nucleic acids, proteins, antibodies, antigens, ligands, receptors, hormones and synthetic compounds. In one aspect of the present invention, novel labeling reagents are disclosed that comprise oligomers or polymers that comprise:

a) two or more labeled moieties where the label or labels are chemically linked to the oligomer or polymer b) one or more reactive groups and c) one or more charged groups that (i) are chemically linked to the oligomer or polymer or (ii) comprise part of the backbone of the oligomer or polymer or (iii) are any combination of the foregoing. When the novel labeling composition or reagent is used to label a compound for detection of a specific analyte, the oligomer or polymer should substantially lack a specific affinity for the analyte.

The multiple labeled groups should increase the amount of signal that is added to the analyte specific moiety; the presence of reactive groups will allow attachment of the multiple labeled groups to a desirable target and the presence of a charged group should allow maintenance or an increase of solubility. Examples of useful chemical linkages for joining labels or charged groups to the oligomer or polymer can include but not be limited to covalent bonds, non-covalent bonds, ionic bonds, ligands, receptors and complexes. Examples of labels or markers can include but not be limited to fluorescent compounds or fluorophores, phosphorescent compounds, chemiluminescent compounds, chelating compounds, electron dense compounds, magnetic compounds, intercalating compounds and energy transfer compounds. With reference to solubility, many fluorescent compounds used as labels have extensive aromatic or hydrophobic character and the charge group or groups of the present invention can provide compensation for this property. Examples of charged groups that may be useful in providing solubility can include but not be limited to phosphate, carboxylic, sulfone, amine and hydroxy groups. The charged groups can be an inherent part of the oligomer or polymer or they can be non-inherent modifications that are artificially introduced. Novel labeled analyte specific moieties may be used for the detection of any analyte including but not limited to nucleic acids, proteins, antibodies, antigens, ligands, receptors, hormones and drugs.

Each of the monomeric units of the oligomer or polymer can comprise a marker or the oligomer or polymer may comprise a mixture of labeled and unlabeled monomeric units. A labeled monomeric unit can comprise a single label or more than one label. When more than one label is included in a monomeric unit, they may be attached at the same site or at different sites on the monomer. An example of a monomeric unit with more than one label at a single site is a nucleotide that has a composite dye such as a fluorescein moiety linked to rhodamine moiety. On the other hand, the same methods used for making a composite dye described in U.S. Patent Publication No. 2005/0137388, incorporated herein by reference, could be applied to the synthesis of tandem dimers, trimers etc. of the same dye. As such, the user is able to direct the number of monomeric units, the proportion of labeled monomeric units, and the number of labels per monomer.

Examples of monomeric units that can be used to create an oligomeric or polymeric labeling reagent can include but not be limited to amino acids, nucleotides, carbohydrates, sugars, aromatic compounds and any organic compound that may be derivatized to be able to form oligomeric or polymeric moieties. Modified versions or analogs of any monomeric units may also be used. Examples of analogs that might find use in the present invention can comprise but not be limited to nucleotide analogs comprising universal or degenerate bases (reviewed in Lockahart 2001, Nucl Acids Res 29:2437-2447), peptide nucleic acid monomers (Nielsen et al., 1991 Science 254:1497), non-nucleotide spacer groups (U.S. Pat. No. 5,696,251), sugar analogs (Ono et al., 1997 Nucl Acids Res 25:4581-4588), methylphosphonamidites (Loschner and Engels 1988 Nucleosides Nucleotides 7:729) and phosphorothioates (Stec et al., 1984 J Am. Chem. Soc. 106:6077) all of which are incorporated by reference.

Examples of oligomers or polymers made from such monomeric units can include but not be limited to nucleic acids, abasic nucleic acids, peptide nucleic acids, polypeptides, proteins, oligosaccharides, polysaccharides and organic polymers. The oligomers or polymers used in the present invention may be isolated from biological sources or they may be created synthetically or in vitro. It may be desirable that the labels and/or reactive groups that are chemically linked to the oligomers or polymers are not intrinsic to such oligomers and polymers. The oligomers or polymers may be homopolymeric and comprise multiples of only one particular type of monomeric unit or they may be heteropolymeric or chimeric and comprise different monomeric units. For example, a chimeric oligomer or polymer can be a nucleic acid construct that comprises both a normal nucleic acid segment and a peptide nucleic acid segment, a combination of nucleotides and amino acids or a combination of a segment of an abasic nucleic acid and a segment comprising a peptide nucleic acid. The present invention finds especial use when the labeling reagent of the present invention is used to label an oligomeric or polymeric target molecule, where the monomeric units of the labeling reagent may have a different nature from the monomeric units of the oligomeric or polymeric target. As an example of this, the oligomeric or polymeric moieties can be nucleic acid constructs that comprise labeled nucleotides or nucleotide analogs and at least one reactive group thereby providing the ability to attach multiple labels to one or more of the amino acids that make up a target protein. Any of the markers, linkers and reactive groups that had been disclosed previously in the literature may find use in this particular embodiment of the present invention.

Additionally, even when the monomeric units of an oligomer or polymer may be of a similar nature, they may be the same or they may be different. For instance a nucleic acid polymer may be a homopolymer comprising a reiteration of a single base or it can be a heteropolymer having varied nucleotides. A polypeptide may be homopolymeric and comprise multiples of a single amino acid or it may be heteropolymeric and comprise different amino acids. The labels in an oligomeric or polymeric labeling reagent may also be the same or they may be different. For instance, a labeling reagent that comprises two different dyes attached at discrete intervals on a polynucleotide may participate in energy transfer for signal generation.

Oligomers or polymers of the present invention may comprise a single chain structure linking the monomeric units together or they may comprise more than one chain. For example, branched, double-stranded and triple-stranded nucleic acids may all find use with present invention. Such multi-chain structures may provide useful properties. For example, a double-stranded nucleic acid is more rigid than a single stranded nucleic acid. The use of a double-stranded structure may allow better control over the distribution or spacing of labeled moieties where proximity or lack of proximity may be desirable. For instance, efficient signal generation by means of energy transfer depends upon a close proximity of donor and acceptor moieties and as such, establishment of a proximity between these moieties can be beneficial. On the other hand, if a single dye species is being used as signal generators, a close proximity of some dye molecules can lead to a self-quenching phenomenon and spreading out the locations of the dyes could be beneficial. The use of more than one chain may also convey other useful properties such as increasing the amount of signal generated or increasing the charge number. Multiple chains may also endow the system with flexibility of use. For example, a first nucleic acid strand may comprise a reactive group and a second nucleic acid strand with complementary sequences can comprise signal groups. By complementary base pairing between these strands, a complex can be formed that comprises a reactive group and signaling groups. To illustrate these points further, some variations on the use of multiple chains are shown in FIG. 1. The use of multiple chains for the novel labeling reagent of the present invention can be extended further in preparation of reagents or labeled moieties that can be used in parallel. For instance, a first chain comprising a reactive group can be mixed with either of two second chains to prepare two different compounds that use the same reactive group but comprised different labels from each other. The oligomers and polymers of the present invention may also comprise non-polymeric components as well. For example, they may comprise termini or extended chains with extended multiple charged groups. Other groups that may offer useful additional properties may also find use with the present invention.

Previous art has disclosed the use of nucleic acids as labeling agents for proteins (U.S. Patent Publication 2010/0273145). However, the methods in that reference described the attachment of an unlabeled polynucleotide to targets followed by hybridization of labeled complementary nucleic acids. In contrast, in the present invention, when a complex comprising two or more oligonucleotides or polynucleotides is used to convey multiple signals, a preformed reagent is used that comprise the signals as well as one or more reactive groups. In this way, the target doesn't proceed through a hybridization reaction. The methodology also allows purification of the complex prior to attachment to a target insuring that there is maximal amount of labeled nucleic strands in the complexes with reactive groups. Due to an interest in labeling nucleic acids, a wide variety of techniques are known in the art for joining nucleic acids to non-nucleic acids. Examples of such methods are disclosed in Jablonski et al., 1986 Nucl acids Res 14; 6115-6128, U.S. Patent Publications 2004/0161741 and 2010/0273145, and "Methods for Nonradioactive Labeling of Nucleic Acids" by Christopher Kessler pp 42-109 in *Nonisotopic Probing,*

*Blotting and Sequencing*, 2$^{nd}$ edition, Larry J. Kricka (Ed.), 1995, Academic Press, Inc., San Diego, Calif., all of which are hereby incorporated by reference.

It is a further aspect of the present invention that when the oligomer or polymer is a nucleic acid, the reactive group may be replaced by a binding partner. Thus, the interaction of a binding partner in the labeling reagent with its binding partner counterpart on the target molecule will allow attachment of the labels to the target molecule. Examples of binding partner pairs can include but not be limited to ligand/receptor, hormone/receptor, biotin/avidin, biotin/streptavidin and antigen/antibody pairs.

As such, in this aspect of the present invention, a novel labeling reagent is disclosed that comprises a nucleic acid strand or a complex of nucleic acid strands which further comprises two or more labels and one or more binding partners where the binding partners may be different from the labels or they may be the same. This aspect of the present invention finds especial use where the labeled nucleic acid strand or complex is linked to a non-nucleic acid target by means of a binding partner. Thus although previous art has described the ability to label nucleic acids by binding labeled proteins, this aspect of the present invention discloses the ability to label proteins by binding labeled nucleic acids.

In a further aspect of the present invention, the novel or oligomeric or polymeric units comprise one or more reactive groups R which may be connected by linker arm L which is a chain of atoms of any length that may be comprised of carbon, nitrogen, oxygen, sulfur in any combination and any other possible atom. The connecting chain can be saturated, unsaturated or can contain aromatic rings and the linking chain can be flexible or rigid. The connecting chain can further comprise any of the rigid units previously disclosed in U.S. Patent Publication 2005/0137388. In this aspect of the invention, examples of reactive groups can include but not be limited to active esters, groups capable of forming a carbon-carbon bonds and groups capable of forming bonds with O, N or S. Examples of such groups can include but not be limited to isothiocyanate, isocyanate, monochlorotriazine, dichlorotriazine, mono- or di-halogen substituted pyridine, mono- or di-halogen substituted diazine, maleimide, aziridine, sulfonyl halogen substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal, aldehyde, carbon-carbon double bonds, mercury salts, and any group capable of reacting with carbon-carbon double bonds, amines, hydroxyl groups, sulfhydryl groups and halogens. The reactive groups may also participate in formation of a coordinate bond when R comprises a ligand or a metal. A reactive group R can be attached to the oligomeric or polymeric moiety through a linker arm L as described above or if desired it may be attached directly without the use of a linker arm. It is a further aspect of this invention that the reactive group can be chemically linked to the novel labeling reagent at a terminus, a side chain or an internal site of the oligomeric or polymeric moiety. Furthermore, the novel polymeric composition described may also contain additional alkyl, aryl and/or polar or charged groups on the backbone, linking arm or the dyes or labels. The polar or charged groups may include but are not limited to halogen, substituted or unsubstituted alkyl or aryl groups, saturated or unsaturated alkyl groups, alkoxy, phenoxy, amino, amido, and carboxyl groups, polar groups such as nitrates, sulfonates, sulfhydryl groups, nitrites, carboxylic acids, phosphates or any other such group or substitutent.

In another aspect of the present invention, the novel oligomeric or polymeric labeling reagents can be described as follows:

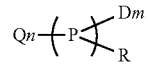

In the diagram above, Q refers to a charged group and n is equal to an integer of 1 or greater; D refers to a dye or other suitable label and m is equal to or greater than 2; R refers to at least one reactive group that may be used to join the labeling reagent to a suitable target and P represents the oligomer or polymer. The charged groups and dyes may be attached to each of the monomeric units that comprise P or only some of the monomeric units may comprise these groups.

In another aspect of the present invention, the novel oligomeric or polymeric labeling reagents can be described as follows:

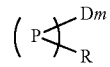

In the diagram above, D refers to a dye or other suitable label and m is equal to or greater than 2; R refers to at least one reactive group; P represents the oligomer or polymer and where D or one of the monomeric units of P comprises one or more charged groups. The dyes may be attached to each of the monomeric units that comprise P or only some of the monomeric units may comprise these groups.

In another aspect of the present invention, novel compositions of the form shown below are disclosed where the novel oligomeric or polymeric labeling reagents of the present invention have been used to label suitable target molecules.

In the diagram above, Q refers to a charged group and n is equal to an integer of 1 or greater; D refers to a dye or other suitable label and m is equal to or greater than 2; P represents an oligomer or polymer; and L is the linkage that joins the labeling reagent to the target molecule. The charged groups and dyes may be attached to each of the monomeric units that comprise P or only some of the monomeric units may comprise these groups. L may comprise any of the linkage arms described previously or it may comprise the linkage formed between a reactive group R and the appropriate chemical group on the target molecule. The target can be chosen from a group that includes but is not limited to peptides, proteins, antibodies, enzymes, enzyme substrates, ligands, hormones, receptors, antigens, haptens, lectins, avidin, streptavidin, lipids, lipoproteins, glycoproteins, proteoglycans, nonpolymeric organic compounds, toxins, carbohydrates, oligosaccharides, polysaccharides, ribonucleotides, deoxyribonucleotides, dideoxyribonucleotides, analogs of deoxynucleotides, ribonucleotides and dideoxynucleotides, modified deoxynucleotides, modified ribonucleotides, modified dideoxynucleotides oligonucleotides, polynucleotides, and any other analyte specific moiety that can form a linkage with the reactive group R.

In another aspect of the present invention, novel compositions of the form shown below are disclosed where the novel oligomeric or polymeric labeling reagents of the present invention have been used to label suitable target molecules:

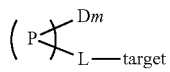

In the diagram above, D refers to a dye or other suitable label and m is equal to or greater than 2; P represents an oligomer or polymer; L is the linkage that joins the labeling reagent to the target molecule and where D or one of the monomeric units of P comprises one or more charged groups. The dyes may be attached to each of the monomeric units that comprise P or only some of the monomeric units may comprise these groups. L may comprise any of the linkage arms described previously or it may comprise the linkage formed between a reactive group R and the appropriate chemical group on the target molecule. The target may be chosen from any members of the group described previously.

The various aspects of the present invention that provide multiple signals allow the synthesis of highly sensitive labeling compositions. In methods previously used for preparing labeled reagents such as enzymatic incorporation, the number of dye units is often limited because of poor incorporation of the dye by the enzyme. Furthermore, it is also possible for two or more dye units to be placed adjacent to each other after enzymatic incorporation, which often results in the quenching of the signal. One advantage of the present invention is that the placement of the dyes can be specifically controlled so that the required number of dye units and spacing between them can be designed for optimal signal. This can result in labeling reagents with labeled units that produce the maximum amount of signal with minimal quenching from adjacent units. The novel labeling reagents of the present invention can be used for a wide variety of purposes where increased signal strength is beneficial.

It is a further aim of the present invention to provide unlabeled reagents that can be used in conjunction with the present invention or with other labeling reagents or labeled materials. For instance, when a compound comprises a target specific moiety and a label, the highest level of signal to noise (S/N) is achieved when binding takes place through the agency of the target specific moiety and not through the label itself, or any components used to join the label to the target specific moiety. By definition, any part of the compound that is not target specific is incapable of discrimination and binding of such moieties to non-target molecules could potentially lead to a rise in background signal generation and a subsequent lowering of the S/N ratio. Therefore, the present invention discloses that unlabeled oligomeric and polymeric compounds that are similar to labeled oligomeric or polymeric moieties used to label target specific moieties can be used in assays detecting the presence or quantity of a particular analyte where the unlabeled oligomers or polymers can suppress non-specific binding by the oligomers or polymeric components of labeled compounds.

As an illustrative example of this method, an antibody labeled with an oligonucleotide comprising multiple fluorescent moieties, e.g., fluorescein, Texas Red, TAMRA (tetramethyl rhodamine), or rhodamine 110, is used as a detection reagent. Nonspecific binding can be blocked by any means known in the art, for example with unlabeled oligonucleotides, or with control oligonucleotides incorporating nonfluorescent analogs of the fluorescent moieties, e.g., O,O-dimethyl fluorescein, N,N-diacetyl rhodamine 110. The blocking reagent can be used either prior to or during exposure of the specimen to the antibody detection reagent. The nucleic acid can be a heterogeneous collection of sequences. For instance, salmon sperm or calf thymus DNA has commonly been used in assays with labeled DNA probes to eliminate non-specific general binding of nucleic acids. Conversely, the sequence of the nucleic acid used to label the antibody could also be used for a blocking reagent, i.e. a discrete sequence. It is also understood that combinations or mixtures of discrete, random, permutational or heterogeneous nucleic acids may be used for this purpose.

Also provided herewith are compounds useful for labeling nucleic acids. The compounds utilize DNA supramolecular binding molecules, which are compounds that non-covalently bind to DNA, where the binding is not by Watson-Crick complementary pairing. Nonlimiting examples of DNA supramolecular binding molecules are minor groove binders, major groove binders, and intercalators. See, e.g., Hannon, 2007, Chem. Soc. Rev. 36:280-295. These molecules bind to DNA, in some cases at specific sequences, often with a high binding affinity. The present invention provides two DNA supramolecular binding molecules covalently joined to each other and further comprising a detectable label. By joining two DNA supramolecular binding molecules together such that both molecules can bind DNA, the binding affinity of the dimer for DNA increases over the binding affinity of each individual molecule, such that the compound displays very tight DNA binding. See, e.g., Capelle et al., 1979, Biochemistry 18:3354-3362. Although many DNA supramolecular binding molecules are fluorescent such that they can serve as a label themselves, the detectable label included with the two DNA supramolecular binding molecules in the present invention allows for the provision of any desired label. The resulting molecule, when combined with the appropriate nucleic acid, spontaneously binds very tightly to the nucleic acid with the desired label. These compounds thus provide a reagent that easily labels nucleic acids with any desired label.

Thus, in various embodiments, the present invention is directed to a compound comprising two DNA supramolecular binding molecules covalently joined by a linker group. In these embodiments, the compound further comprises a detectable label bound thereto, where the detectable label is not either of the two DNA supramolecular binding molecules.

In some embodiments, at least one of the DNA supramolecular binding molecules is a minor groove binder. Any minor groove binders known in the art can be used in these compounds. In some embodiments, the minor groove binder is a diacrylamidine, or a bis-benzimidazole. In more specific embodiments, the minor groove binder is DAPI, berenil, pentamidine, distamycin A, or Hoechst 33258.

In other embodiments, at least one of the DNA supramolecular binding molecules is a major groove binder. Any major groove binder can be utilized in these embodiments. Nonlimiting examples include a molecule comprising a zinc finger, a leucine zipper or a helix-turn-helix motif.

In additional embodiments, at least one of the DNA supramolecular binding molecules is an intercalator. Publications describing the use of intercalating dyes in studies using nucleic acids include Georghiou, Photochem. Photobiol. 26:59-68 (1977); Kubota et al., Biophys. Chem., 6:279-

284 (1977); Genest et al., Nucl. Acid Res., 13:2603-2615 (1985); Asseline, EMBO J. 3:795-800 (1984); and U.S. Pat. Nos. 4,257,774 and 4,547,569.

In some of these embodiments, both of the DNA supramolecular binding molecules are intercalators, either the same or different intercalators.

These embodiments are not narrowly limited to any particular DNA intercalators. Nonlimiting examples of classes of intercalators that may be used in these embodiments are acridines, coumarins, psoralens, quinoxalines, phenanthridines, anthracyclines, or metallo-intercalators, as they are known in the art (see, e.g., Hannon et al., Id.). Particular useful intercalators include 9-aminoacridine, 7-hydroxy-4-methylcoumarin, 7-amino-4-methylcoumarin, 4-methyl-7-sulphato-methylcoumarin, 8-[[[(diethylamino)methyl]propyl]oxy]psoralen, 5(N-piperadinyl)-8-methoxypsoralen, ethidium bromide, thiazole orange, 6-(-4'-carboxyphenyl)-3,8-diamine-5-methyl phenanthridinium chloride, doxorubicin, daunomycin, [Pt(tpy)(SCH$_2$CH$_2$OH)]$^+$, and [Rh(phi)(Me$_2$trien)]$^{3+}$.

The linker in these compounds not only links the two DNA supramolecular binding molecules but can also serve to separate the two molecules so that both of the molecules can bind to a nucleic acid. For example, it is well known that DNA intercalators can be inserted into DNA at a maximum of one intercalator per two basepairs. Consequently, where two intercalators are used with these compounds, the linker preferably separates those intercalators at a distance of at least two basepairs, so that they can both insert into the nucleic acid. Such linkers are known in the art and have been utilized with several dimeric intercalators. See, e.g., Canellakis and Bellantone, 1976, Biochim. Biophys. Acta 418: 290-299; Canellakis et al., 1976, Biochemical Pharmacol. 25:231-236; Canellakis et al., 1976, Biochim. Biophys. Acta 418:277-289; Canellakis et al., 1976, Biochim. Biophys. Acta 418:300-314; Fico et al., 1977, Science 198:53-56; Wakelin et al., 1978, Biochemistry 17:5057-5063; Gaugain et al., 1978, Biochemistry 17:5071-5087; Gaugain et al., 1978, Biochemistry 17:5078-5088; Chen et al., 1978, J. Medicinal Chem. 21:868-874; Capelle et al., 1979, Biochemistry 18:3354-3362; Wright et al., 1980, Biochemistry 19:5825-2836; King et al., 1982, Biochemistry 21:4982-4989; Timtcheva et al., 2000, J. Photochem. Photobiol. B:Biology 58:130-135; Moloney et al., 2001, Molecules 6:230-243.

Similar considerations apply to other DNA supramolecular binding molecules—the linker is preferably of sufficient length so that both molecules can bind to a nucleic acid.

The linker in these compounds can be rigid or flexible. Rigid linkers have been utilized with dimer intercalators. See, e.g., Glover et al., 2003, J. Am. Chem. Soc. 125:9918-9919. However, flexible linkers do not require the precise design required of rigid linkers, where the linker must precisely separate and orient the DNA supramolecular binding molecules to properly insert into the nucleic acid.

In some embodiments, the linker is an unsubstituted $C_1$-$C_{20}$ straight-chain, branched or cyclic alkyl, alkenyl or alkynyl group, a substituted $C_1$-$C_{20}$ straight-chain, branched or cyclic alkyl, alkenyl or alkynyl group wherein one or more C, CH or CH$_2$ groups are substituted with an O atom, N atom, S atom, NH group, CO group or OCO group, or an unsubstituted or substituted aromatic group. In more specific embodiments, the linker is —(CH$_2$)$_{1-10}$—NH—(CH$_2$)$_{1-10}$—. In still more specific embodiments, the linker is —(CH$_2$)$_{1-5}$—NH—(CH$_2$)$_{1-5}$—. One useful linker within these embodiments is —(CH$_2$)$_3$—NH—(CH$_2$)$_4$— (spermidine—see Examples 20-22 and the exemplary compounds described below).

Any detectable label now known or later discovered may be utilized for these compounds. In some embodiments, the detectable label is radioactive. The radioactive label can be part of the compound (e.g., $^3$H, or $^{14}$C), or can be attached thereto (e.g., $^{131}$I).

In other embodiments, the detectable label is non-radioactive. Non-limiting examples include fluorescent compounds, phosphorescent compounds, chemiluminescent compounds, chelating compounds, electron dense compounds, magnetic compounds, and energy transfer compounds, as they are known in the art.

In various embodiments, the non-radioactive detectable label is a fluorophore. Any fluorophore now known or later discovered can be utilized in these compounds. Examples of useful fluorophores include without limitation a symmetric or asymmetric cyanine dye, a merocyanine dye, a styryl dye, an oxazine dye, a xanthene dye, a coumarin dye or an iminocoumarin dye.

One class of fluorophore useful in the invention has a xanthene backbone shown in Scheme I below. The structures are shown in their lactone forms (A) as well as aphenylic counterparts, which have their appended phenyl ring missing (B).

Scheme I

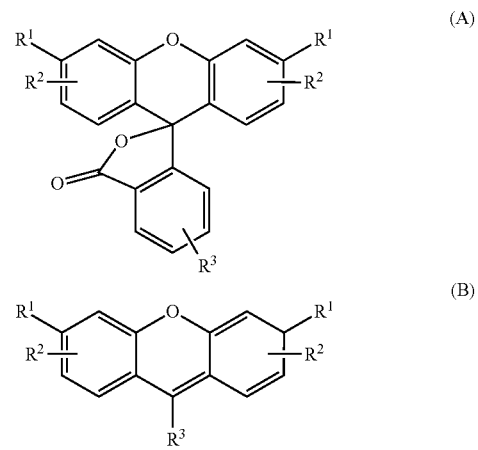

The substituents $R^1$, $R^2$ and $R^3$ in Scheme I represent a variety of functionalities where $R^3$ may be a reactive group, which allows the attachment to other moieties, e.g., the linker. The $R^1$ and $R^2$s may be structurally the same or different; there may be more than one $R^2$ on either or both rings. An IC group can join with an $R^1$ group to form a ring. Suitable examples of $R^1$ include but are not limited to hydrogen, OH, OR$^4$, NH$_2$, NHR$^4$, or NR$^4$R$^4$ where each R$^4$ is independently a straight-chain, branched or cyclic $C_1$-$C_5$ alkyl group, optionally further comprising a carboxyl or carbonyl (COR$^5$) group, where R$^5$ is hydrogen, an optionally substituted straight-chain, branched or cyclic alkyl, alkenyl or alkynyl group, where one or more C, CH or CH$_2$ groups can be replaced with an O atom, an N atom, an S atom, a NH group, a CO group, an OCO group, a CONR$^6$ group, or an optionally substituted aromatic group, where R$^6$ is a straight-chain, branched or cyclic alkyl, alkenyl or alkynyl group. Suitable examples of $R^2$ and $R^3$ include but are not limited to hydrogen, a halogen (F, Cl, Br, I), a cyano group (CN), a nitro group (NO²), an isocyano group (NC), a thiocyano group (SCN), an isothiocyano group (SNC), a sulfonate group ($SO_3R^7$), a sulfate group ($SO_3R^7$), a carboxyl group ($CO_2H$), an ester group ($CO_2R^7$ or $OCOR^7$), an amide group ($CONR^6_2$ or $NR^6COR^7$), a carbamate group ($NR^7CO_2R^7$ or $OCONR^7_2$), a phosphate group ($OPO_3R^7_3$), a phosphonate group ($PO_3R^7_2$), an alkoxy group ($OR^7$), a sulfoxy group ($SOR^7$), a sulfone group ($SO_2R^7$), a sulfonamide group ($SO_2NR^7_2$), an optionally substituted straight-chain, branched or cyclic alkyl, alkenyl or alkynyl group wherein one or more C, CH or $CH_2$ groups can be replaced with O atom, N atom, CO group, OCO group, CONIC group, or an optionally substituted aromatic group. In these embodiments, each $R^7$ is independently hydrogen, an optionally substituted straight-chain, branched or cyclic alkyl, alkenyl or alkynyl group wherein one or more C, CH or $CH_2$ groups can be replaced with O atom, N atom, CO group, OCO group, $CONR^6$ group, or an optionally substituted aromatic group.

As discussed above, the $R^3$ group is, or can be substituted to contain, a reactive group thereby allowing the fluorophore to be chemically bound to the linker or one or both intercalators. Examples of reactive groups that may find use in the present invention can include but not be limited to a nucleophilic reactive group, an electrophilic reactive group, a terminal alkene, a terminal alkyne, a platinum coordinate group or an alkylating agent.

There are a number of different electrophilic reactive groups that may find use in these embodiments. Examples include but not be limited to isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-proprionamide, glyoxal and aldehyde groups. Nucleophilic reactive groups can include but not be limited to reactive thiol, amine and hydroxyl groups. For purposes of synthesis of dyes, reactive thiol, amine or hydroxyl groups can be protected during various synthetic steps and the reactive groups generated after removal of the protective group.

One class of xanthene fluorophores useful in the present invention includes but not limited to rhodamine and rhodamine derivatives, such as Pennsylvania Green, Tokyo Green, Oregon Green, Singapore Green, and rosamines and rhodols and their derivatives. Some of these derivatives are shown below in Scheme II. The rhodamine, rosamine and rhodol backbone structures can be extended by adding additional rings as shown in Scheme III, or their appended phenyl ring might be missing to form aphenylic counterparts.

Scheme II

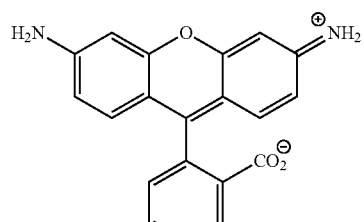

Rhodamine 110

-continued

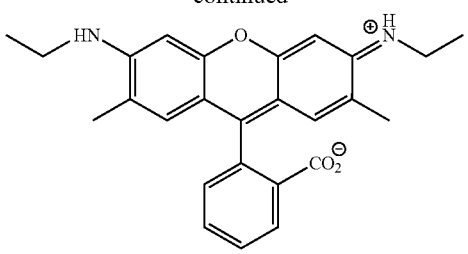

Rhodamine 575

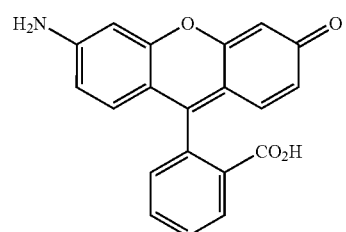

Rhodol

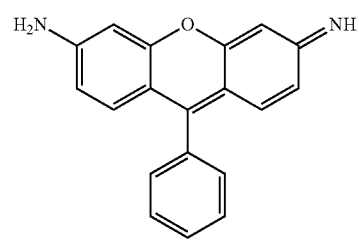

Rosamine

Scheme III

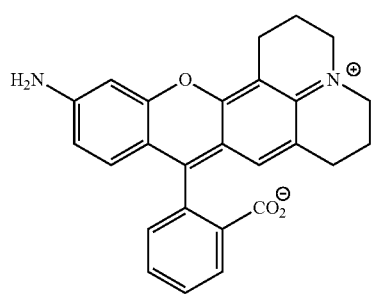

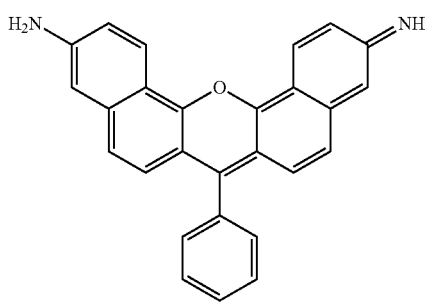 [SMILES: N=c1ccc2c(ccc3c(-c4ccccc4)c4ccc5cc(N)ccc5c4oc32)c1]

Another class of fluorescent dyes pertinent to the present invention is based on coumarin and iminocoumarin backbone structure shown in Scheme IV.

Scheme IV

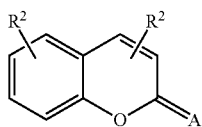

The substituent R² in Scheme IV represents functionalities defined in Scheme I above while A can be an O atom, or imino group, NH. Some of the compounds in this category are shown below in Scheme V. The backbone structure can be extended by adding additional rings, aliphatic or aromatic, substituted or unsubstituted.

Scheme V

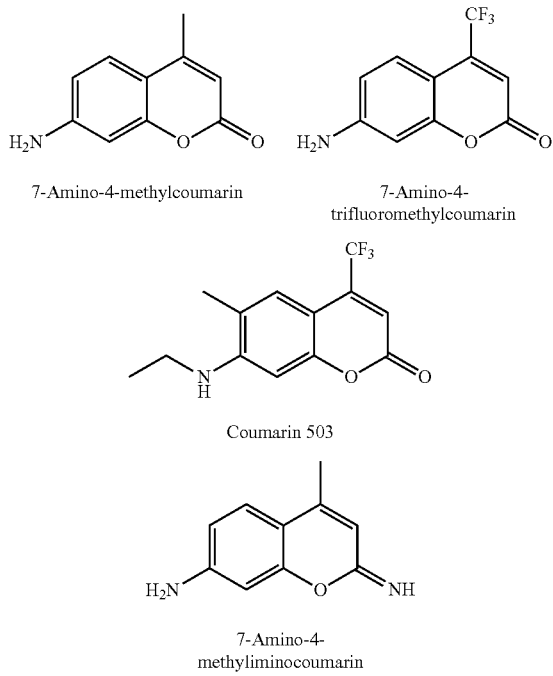

7-Amino-4-methylcoumarin

7-Amino-4-trifluoromethylcoumarin

Coumarin 503

7-Amino-4-methyliminocoumarin

In other embodiments of the compounds of the present invention, the detectable label is a luminescent moiety. Any luminescent moiety, including any chemiluminescent or bioluminescent moieties, now known or later discovered, can be utilized in these embodiments. In some aspects of these embodiments, the compound comprises the structure:

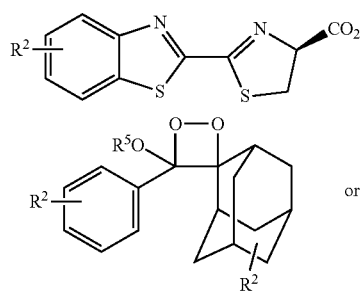

or

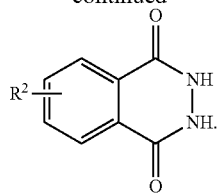

The substituents R² and R⁵ in these structures represent functionalities defined in Scheme I above.

In some embodiments, the detectable label is bound to the compound via a binding pair. A multitude of binding pairs is known in the art. Nonlimiting examples include ligand/receptors, hormone/receptors, biotin/avidin, biotin/streptavidin, and antigen/antibodies.

In other embodiments, the detectable label is covalently bound to the compound, either to the linker group or to one or both of the DNA supramolecular binding molecules. When bound to a DNA supramolecular binding molecule, it is preferred that the detectable label does not interfere, e.g., through steric hindrance, with the ability of the DNA supramolecular binding molecule to bind to nucleic acids.

In various embodiments, these compounds comprise more than two DNA supramolecular binding molecules and/or more than one detectable label.

Exemplary compounds comprising two intercalators and fluorescent labels are

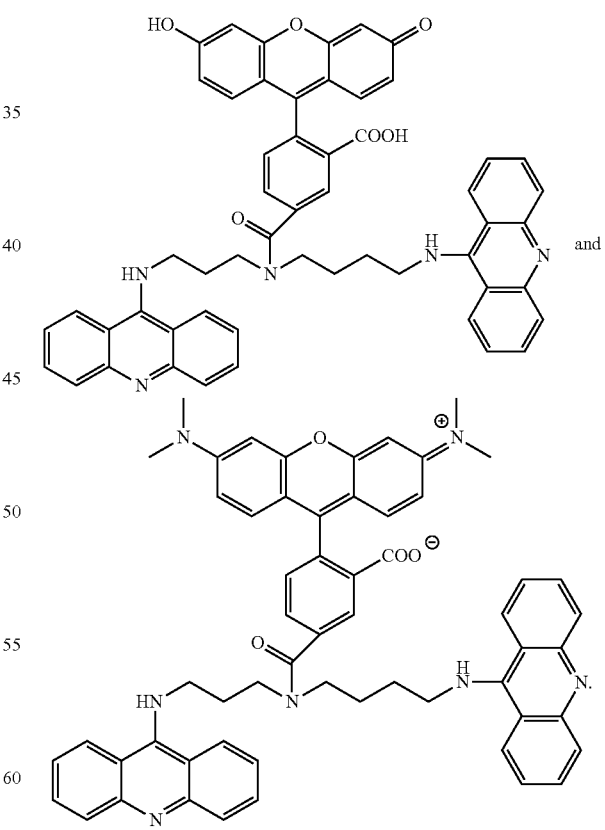

and

The ease with which the multisignal labeling reagents described herein can be synthesized is directly related to the ease of binding the detectable labels to the reagents. In this regard, DNA supramolecular binding molecules bind spontaneously without any modification of the nucleic acid that makes up the backbone of various multisignal labeling reagents. This spontaneous binding of DNA supramolecular binding molecules forms the basis of particular embodiments of the instant invention.

Thus, provided is a multisignal labeling reagent that comprises (i) an oligomer of nucleotides or nucleotide analogs; (ii) a DNA supramolecular binding molecule noncovalently bound to the oligomer; and (iii) a covalently bound first reactive group or a first partner of a first binding pair.

In some of these embodiments, the DNA supramolecular binding molecule is fluorescent. Examples include most intercalators and the minor groove binder DAPI. In these embodiments, the DNA supramolecular binding molecule itself can serve as a label, by virtue of its fluorescence. In other embodiments, the DNA supramolecular binding molecule further comprises a detectable label that is not the supramolecular binding molecule. These latter embodiments allow the user to select the label having the desired detection characteristics, such as fluorescence emission maxima.

Any detectable label now known or later discovered may be utilized for these reagents. In some embodiments, the detectable label is radioactive. The radioactive label can be part of the compound (e.g., $^3$H, or $^{14}$C), or can be attached thereto (e.g., $^{131}$I).

In other embodiments, the detectable label is non-radioactive. Non-limiting examples include fluorescent compounds, phosphorescent compounds, chemiluminescent compounds, chelating compounds, electron dense compounds, magnetic compounds, and energy transfer compounds, as they are known in the art.

In various embodiments, the non-radioactive detectable label is a fluorophore. Any fluorophore now known or later discovered can be utilized in these reagents. Examples of useful fluorophores include without limitation a symmetric or asymmetric cyanine dye, a merocyanine dye, a styryl dye, an oxazine dye, a xanthene dye, a coumarin dye or an iminocoumarin dye, as described above.

These multisignal labeling reagents can incorporate any DNA supramolecular binding molecule known in the art. In some embodiments, the DNA supramolecular binding molecule is a minor groove binder. Any minor groove binders known in the art can be used in these reagents. In some embodiments, the minor groove binder is a diacrylamidine, or a bis-benzimidazole. In other embodiments, the minor groove binder is DAPI, berenil, pentamidine, distamycin A, or Hoechst 33258.

In other embodiments, the DNA supramolecular binding molecule is a major groove binder. Any major groove binder can be utilized in these reagents. Nonlimiting examples include a molecule comprising a zinc finger, a leucine zipper or a helix-turn-helix motif.

In additional embodiments, the DNA supramolecular binding molecule is an intercalator, as described above. In some of these embodiments, the intercalator is an acridine, a coumarin, a psoralen, a phenanthridine, an anthracycline, or a metallo-intercalator. Particular useful intercalators include 9-aminoacridine, 7-hydroxy-4-methylcoumarin, 7-amino-4-methylcoumarin, 4-methyl-7-sulphato-methyl-coumarin, 8-[[[(diethylamino)methyl]propyl]oxy]psoralen, 5(N-piperadinyl)-8-methoxypsoralen, ethidium bromide, thiazole orange, 6-(-4'-carboxyphenyl)-3,8-diamine-5-methyl phenanthridinium chloride, doxorubicin, daunomycin, [Pt(tpy)(SCH$_2$CH$_2$OH)]$^+$, and [Rh(phi)(Me$_2$trien)]$^{3+}$.

It is envisioned that, in most cases, the multisignal labeling reagents provided here comprise multiple DNA supramolecular binding molecules. The multiple DNA supramolecular binding molecules on any particular multisignal labeling reagent may be any combination of any DNA supramolecular binding molecule or may be all the same DNA supramolecular binding molecule. In some embodiments, the multisignal labeling reagent comprises the compound described above comprising two DNA supramolecular binding molecules covalently joined by a linker group.

The oligomer of any multisignal labeling reagent described herein can be any form of nucleic acid or analog, provided the DNA supramolecular binding molecule can bind thereto. Additionally, the oligomer can be any length, for example less than 10 nucleotides, less than 20 nucleotides, less than 50 nucleotides, less than 100 nucleotides, or 100 or more nucleotides.

Many DNA supramolecular binding molecules bind DNA in a sequence preferential or sequence specific manner. For example, many intercalators have a preference for the AT sequence. See, e.g., Hampshire and Fox, 2008, Anal. Biochem. 374:298-303. Also, major groove binders generally have specific sequence requirements. See, e.g., Christy and Nathans, 1090, Proc. Natl. Acad. Sci. USA 86:8737-8741. Such a sequence preference or requirement should be considered when a nucleic acid that is used for binding of the invention compounds is designed.

The first reactive group or the first partner of the first binding pair of the multisignal labeling reagent described herein may be used to bind the reagent to a target to label the target for detection, as described above. In some embodiments, the multisignal labeling reagent comprises a first partner of a first binding pair. Nonlimiting examples include a ligand/receptor, a hormone/receptor, biotin/avidin, biotin/streptavidin or an antigen/antibody. A preferred first partner of the first binding pair is streptavidin. In other embodiments, the multisignal labeling reagent comprises a first reactive group, as described above.

In some embodiments, particularly where a multisignal labeling reagent comprises only one oligomer, the first reactive group or the first binding partner of the first binding pair is covalently bound to the oligomer. In other embodiments, the multisignal labeling reagent further comprises a polymer to which two or more of the oligomers are bound, where the first reactive group or the first partner of the first binding pair is covalently attached to the polymer. The polymer can be, e.g., a oligopeptide, a protein, a nucleic acid or analog such as an oligonucleotide or a polynucleotide, a lipid, a oligosaccharide, a polysaccharide, or a synthetic compound such as an organic polymer (e.g., a plastic). In some embodiments, the polymer is a nucleic acid and the two or more oligomers are bound to the polymer by complementary hybridization, for example as illustrated in FIG. 1, diagram (b) or (d).

Also provided herein are methods for producing the multisignaling labeling reagents described above. These methods provide for the use of a primer, template, polymerase and labeled nucleotide triphosphates (NTPs) or analogs to prepare the oligonucleotide of the reagents, by hybridizing the primer to the template and extending the primer along the template using NTPs, at least one of which is labeled. One aspect of these methods, where the labeled oligonucleotide comprises a streptavidin for binding directly to a target molecule, is illustrated in FIG. 2; examples of these methods are provided in Examples 18 and 19. These methods fall in two general categories: (1) where a single oligonucleotide comprising more than one label is designed to bind to the target molecule; and (2) where multiple oligonucleotides, each comprising more than one label, is bound to a polymer, where the polymer is designed to bind to the target molecule. In these methods, the single oligonucleotide (category 1) or polymer comprising multiple labeled oligonucleotides (category 2) is designed to bind to the target molecule through either a reactive group (termed "first reactive group" in these methods) or through a binding pair, where one partner of the binding pair ("first partner of a first binding pair") (e.g., streptavidin) is bound to the multisignal labeling reagent, and the other partner of the binding pair (e.g., biotin) is bound to the target molecule. This provides a branched multisignal labeling reagent, for example as illustrated in FIG. 1 and exemplified in Example 19.

It is also to be recognized that in these methods, the detectable label (e.g., a fluorescent dye) can be covalently bound to the NTPs or analogs during the primer extension procedure. Alternatively, the NTPs or analogs can comprise a reactive group ("second reactive group" herein) or a partner of a binding pair ("first partner of a second reactive group") (e.g., biotin), to which the detectable label is attached after synthesis of the oligonucleotide (as described in steps (A) and (B) in the methods provided below).

Thus, in some embodiments, a method of producing a multisignal labeling reagent is provided. The method comprises (a) obtaining
  (i) a primer comprising an oligonucleotide and a first reactive group or a first partner of a first binding pair at the 5' end of the oligonucleotide;
  (ii) a template comprising a nucleic acid comprising a first sequence that is complementary to the oligonucleotide and a second sequence that extends in the 5' direction from the first sequence;
  (iii) a polymerase capable of extending the oligonucleotide along the template nucleic acid when the template nucleic acid is hybridized to the oligonucleotide at the first sequence; and
  (iv) nucleotide triphosphates (NTPs) or analogs thereof that are capable of being incorporated into the extended oligonucleotide, wherein at least one of the NTPs or analogs comprises a non-radioactive detectable label, a second reactive group or a first partner of a second binding pair; and
(b) combining the primer, template, polymerase and NTPs or analogs under conditions such that the oligonucleotide hybridizes to the first sequence and is extended along the second sequence, where the extended oligonucleotide comprises at least two NTPs or analogs incorporated therein that comprise a non-radioactive detectable label, a second reactive group or a first partner of a second binding pair;
wherein,
  (A) if at least one of the two or more NTPs or analogs incorporated into the extended oligonucleotide comprises a second reactive group, the method further comprises combining the extended oligonucleotide with a first compound comprising a non-radioactive detectable label covalently linked to a moiety capable of reacting with the second reactive group such that the label is covalently linked to the extended primer, and
  (B) if at least one of the two or more NTPs or analogs incorporated into the extended oligonucleotide comprises a first partner of the second binding pair, the method further comprises combining the extended primer with a second compound comprising the non-radioactive detectable label covalently linked to a second binding partner of the second binding pair.

This method can utilize any non-radioactive label now known or later discovered. Examples of useful non-radioactive detectable labels are fluorophores, phosphorescent moieties, chemiluminescent moieties, chelating moieties, electron dense moieties, magnetic moieties, or energy transfer moieties, as they are known in the art.

In some embodiments, the non-radioactive detectable labels are fluorophores, e.g., symmetric or asymmetric cyanines, merocyanines, styryl moieties, oxazines, xanthenes, coumarins or iminocoumarins, as detailed above. In other embodiments, the non-radioactive detectable labels are chemiluminescent or phosphorescent moieties, as discussed above.

The oligonucleotide of the multisignaling labeling reagent produced by this method can be comprised of any form of oligonucleotide or analog that can be extended with a polymerase, including DNA, RNA, or analogs thereof. Additionally, the oligonucleotide can be of any length, for example less than 10 nucleotides, less than 20 nucleotides, less than 50 nucleotides, less than 100 nucleotides, or 100 or more nucleotides. Further, any polymerase can be used in these methods, provided the polymerase is capable of extending the primer along the template oligonucleotide.

In this method, the NTPs or analogs that are labeled with the label, second reactive group, or first binding partner of a second binding pair is preferably only one of the four NTPs or analogs used to extend the primer. By using only one labeled NTP or analog of the four NTPs or analogs used to extend the primer, the position of the labels can be precisely controlled by designing the template oligonucleotide such that the planned labeled NTP or analog is at the desired position.

The at least two NTPs or analogs that are labeled on the extended oligonucleotide of the multisignal labeling reagent can be incorporated into the oligonucleotide as NTPs or analogs comprising the detectable labels or with the second reactive group or the first binding partner of the second binding pair.

Where NTPs or analogs comprising the second reactive group are utilized, the detectable label must subsequently be added by adding a compound comprising the non-radioactive detectable label covalently linked to a moiety capable of reacting with the second reactive group such that the label is covalently linked to the extended primer, as indicated in step (A) of the method. Nonlimiting examples of reactive groups useful here include isothiocyanate, isocyanate, monochlorotriazine, dichlorotriazine, mono- or di-halogen substituted pyridine, mono- or di-halogen substituted diazine, maleimide, aziridine, sulfonyl halogen substituted diazine, maleimide, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal, aldehyde, mercury salt, or combinations thereof. Methods of attaching detectable labels to NTPs or analogs in this manner are well known in the art and summarized above.

In some embodiments, each reactive group is connected to the NTPs or analogs by a linker arm, also as described above.

Where NTPs or analogs comprising the first binding partner of the second binding pair are utilized, the detectable label must subsequently be added by combining the extended primer with a compound comprising the non-radioactive detectable label covalently linked to a second binding partner of the second binding pair, as indicated in step (B) of the method. Binding pairs are further discussed above. A nonlimiting example of a first binding partner of the second binding pair is biotin.

In some embodiments, each first binding partner of the second binding pair is connected to the NTPs by a linker arm.

As discussed above in relation to other multisignal labeling reagents, the multisignal labeling reagents described here can comprise a non-inherent charged group that increases the aqueous solubility of the reagent. Nonlimiting examples of such charged groups include phosphate, carboxylic acid, sulfone, amine and hydroxy groups.

As discussed above, the primer comprises a first reactive group or a first partner of a first binding pair, to attach the multisignal labeling reagent to a target. Any reactive group as discussed above may be utilized here. Where the primer comprises a first partner of a first binding pair, any binding pair, now known or later discovered, may be provided with the primer. Examples include a ligand/receptor, a hormone/receptor, biotin/avidin, biotin/streptavidin and an antigen/antibody. A preferred first partner of a first binding pair is streptavidin. See, e.g., Example 18.

For its ultimate use, these methods can further comprise combining the multisignal labeling reagent with a target molecule such that the multisignal labeling reagent is bound to the target by the first reactive group or the first partner of the first binding pair. The target may be any compound to which a detectable label is desired. Nonlimiting examples of targets are peptides, proteins, antibodies, enzymes, enzyme substrates, nonpolymeric organic compounds, ligands, hormones, receptors, antigens, haptens, lectins, carbohydrates, oligosaccharides, polysaccharides, oligonucleotides, polynucleotides, lipids, lipoproteins, glycoproteins, and proteoglycans.

As discussed above, methods utilizing a primer, template, polymerase and labeled NTPs or analogs can be used to prepare a branched multisignal labeling reagent, where more than one extended oligonucleotide with labels are bound to a polymer, as illustrated in FIG. 1, and exemplified in Example 19. These methods comprise (a) obtaining
 (i) a primer comprising an oligonucleotide;
 (ii) a template comprising a nucleic acid comprising a first sequence that is complementary to the oligonucleotide and a second sequence that extends in the 5' direction from the first sequence;
 (iii) a polymerase capable of extending the oligonucleotide along the template nucleic acid when the template nucleic acid is hybridized to the oligonucleotide at the first sequence;
 (iv) nucleotide triphosphates (NTPs) or analogs thereof that are capable of being incorporated into the extended oligonucleotide, wherein at least one of the NTPs or analogs comprises a non-radioactive detectable label, a second reactive group or a first partner of a second binding pair; and
 (v) a polymer capable of binding to more than one of the extended oligonucleotide, wherein the polymer comprises a first reactive group or a first partner of a first binding pair;
(b) combining the primer, template, polymerase and NTPs or analogs under conditions such that the oligonucleotide hybridizes to the first sequence and is extended along the second sequence, where the extended oligonucleotide comprises at least two NTPs or analogs incorporated therein that comprise a non-radioactive detectable label, a second reactive group or a first partner of a second binding pair; and
(c) combining the extended oligonucleotide with the polymer under conditions such that at least two of the extended oligonucleotides bind to the polymer,
 wherein,
 (A) if at least one of the two or more NTPs or analogs incorporated into the extended oligonucleotide comprises a second reactive group, the method further comprises combining the extended oligonucleotide with a first compound comprising a non-radioactive detectable label covalently linked to a moiety capable of reacting with the second reactive group such that the label is covalently linked to the extended primer, and
 (B) if at least one of the two or more NTPs or analogs incorporated into the extended oligonucleotide comprises a first partner of the second binding pair, the method further comprises combining the extended primer with a second compound comprising the non-radioactive detectable label covalently linked to a second binding partner of the second binding pair.

This method can utilize any non-radioactive label now known or later discovered. Examples of useful non-radioactive detectable labels are fluorophores, phosphorescent moieties, chemiluminescent moieties, chelating moieties, electron dense moieties, magnetic moieties, or energy transfer moieties.

In some embodiments, the non-radioactive detectable labels are fluorophores, e.g., symmetric or asymmetric cyanines, merocyanines, styryl moieties, oxazines, xanthenes, coumarins or iminocoumarins, as detailed above. In other embodiments, the non-radioactive detectable labels are chemiluminescent or phosphorescent moieties, as discussed above.

The oligonucleotide of the multisignaling labeling reagent produced by this method can be comprised of any form of oligonucleotide or analog that can be extended with a polymerase, including DNA, RNA, or analogs thereof. Additionally, the oligonucleotide can be of any length, for example less than 10 nucleotides, less than 20 nucleotides, less than 50 nucleotides, less than 100 nucleotides, or 100 or more nucleotides. Further, any polymerase can be used in these methods, provided the polymerase is capable of extending the primer along the template oligonucleotide.

In this method, the NTPs or analogs that are labeled with the label, second reactive group, or first binding partner of a second binding pair is preferably only one of the four NTPs or analogs used to extend the primer, as discussed above in relation to the previously described method.

The at least two NTPs or analogs that are labeled on the extended oligonucleotide of the multisignal labeling reagent can be incorporated into the oligonucleotide as NTPs or analogs comprising the detectable labels or with the second reactive group or the first binding partner of the second binding pair.

Where NTPs or analogs comprising the second reactive group are utilized, the detectable label must subsequently be added by adding a compound comprising the non-radioactive detectable label covalently linked to a moiety capable of reacting with the second reactive group such that the label is covalently linked to the extended primer, as indicated in step (A) of the method. Examples of reactive groups are discussed above.

In some embodiments, each reactive group is connected to the NTPs or analogs by a linker arm, also as described above.

Where NTPs or analogs comprising the first binding partner of the second binding pair are utilized, the detectable label must subsequently be added by combining the extended primer with a compound comprising the non-radioactive detectable label covalently linked to a second binding partner of the second binding pair, as indicated in step (B) of the method. Binding pairs are further discussed above.

In some embodiments, each first binding partner of the second binding pair is connected to the NTPs by a linker arm.

As discussed above in relation to other multisignal labeling reagents, the multisignal labeling reagents described here can comprise a non-inherent charged group that increases the aqueous solubility of the reagent. Nonlimiting examples of such charged groups include phosphate, carboxylic acid, sulfone, amine and hydroxy groups.

The polymer can be any compound to which more than one oligonucleotide (extended primer) can be bound covalently or noncovalently. Nonlimiting examples include oligopeptides, proteins, nucleic acids or analogs such as an oligonucleotide or a polynucleotide, a lipid, a oligosaccharide, a polysaccharide, or a synthetic compound such as an organic polymer (e.g., a plastic). In some embodiments, the polymer is a nucleic acid or analog and the two or more oligomers are bound to the polymer by complementary hybridization. In these embodiments, the polymer can be of any length, for example less than 10 nucleotides, less than 20 nucleotides, less than 50 nucleotides, less than 100 nucleotides, or 100 or more nucleotides.

As discussed above, the polymer comprises a first reactive group or a first partner of a first binding pair, to attach the multisignal labeling reagent to a target. Any reactive group as discussed above may be utilized here. Where the polymer comprises a first partner of a first binding pair, any binding pair, now known or later discovered, may be provided with the polymer. Examples include a ligand/receptor, a hormone/receptor, biotin/avidin, biotin/streptavidin and an antigen/antibody. A preferred first partner of a first binding pair is biotin. See, e.g., Example 19.

For its ultimate use, these methods can further comprise combining the multisignal labeling reagent with a target molecule such that the multisignal labeling reagent is bound to the target by the first reactive group or the first partner of the first binding pair. The target may be any compound to which a detectable label is desired. Nonlimiting examples of targets are peptides, proteins, antibodies, enzymes, enzyme substrates, nonpolymeric organic compounds, ligands, hormones, receptors, antigens, haptens, lectins, carbohydrates, oligosaccharides, polysaccharides, oligonucleotides, polynucleotides, lipids, lipoproteins, glycoproteins, and proteoglycans.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1. Multisignal Labeling Reagent a) a 33-mer oligonucleotide with the following structure is synthesized:

```
                                              (SEQ ID NO: 1)
5'-PO4-T TU* T T T TT U* T T T T T U*  T T T T TU*
T T T T T U* T T T T T U*-3'
``` where the 5' end has a phosphate group and the oligonucleotide comprises allylamine modified Uridine moieties (symbolized as U*).

b) The active ester of tetramethyl rhodamine (TAMRA), rhodamine 110, or the aphenylic Texas Red analogue described in U.S. Pat. No. 7,166,478, can be reacted with the allylamine moieties in the oligonucleotide to produce a labeled oligonucleotide using the same procedures described in that reference for attachment of the TAMRA, rhodamine 110, or aphenylic Texas Red analogue to allylamine modified dUTP.

c) The 5' phosphate of the labeled oligonucleotide is reacted with a primary dialkylamine by the procedure described by Halloran and Parker (1966, J. Immunol 96:373) thereby transforming the labeled oligonucleotide into a multisignal labeling reagent with a 5' amine group.

d) The primary amine at the 5' end is then reacted with a 20 fold molar excess of succinylmaleic acid active ester at pH 7.8 for 45 minutes at room temperature to tether the maleimide group to the 5' end. The pH is immediately adjusted to pH 4-5 by adding concentrated acetic acid and the maleimide derivatized oligonucleotide is precipitated by ethanol. It is then resuspended in LiAc (pH 4) buffer and precipitated again. Before use, the maleimide derivatized oligonucleotide is dissolved in Acetate buffer (pH 5.5). This procedure generates a multisignal labeling reagent that comprises 6 TAMRA, rhodamine 110, or Texas Red dye moieties and a single reactive group for attachment to a desirable target.

Example 2. Use of Multisignal Labeling Reagent with Proteins

The reagent from Example 1 can be used directly to label a protein that has available sulfhydryl groups. For instance, BSA can be labeled at room temperature by reacting it with the maleimide derivatized reagent at pH 5.5.

Example 3. Modification of Proteins for Use with Multisignal Labeling Reagent Proteins that lack available sulfhydryl groups may also be used with the reagent from Example 1. For instance, an antibody can be treated with N-acetyl-homocysteine thiolactone at pH 9 thereby introducing sulfhydryl groups that can be labeled with the maleimide derivatized reagent as described above in Example 2. By varying the reaction time and concentration of the N-acetyl-homocysteine thiolactone, the number of sulfhydryl groups introduced into a protein can be controlled. To retain biological activity, it is preferred that an antibody be modified with at most 2-3 sulfhydryl groups.

Example 4. Modification of Multisignal Labeling Reagent

The multisignal labeling reagent described in step c) of Example 1 is treated with bromoacetic acid NHS ester to tether a bromoacetyl group to the 5' end. This group is very reactionary to primary amines and can be used at pH 9 to label a protein or other desirable group that contains primary amines or thiol groups. As described previously, these groups can be native to the target molecule or introduced.

Example 5. Multisignal Labeling Reagent Used with Glycoprotein

In addition to the amine and sulfhydryl groups described previously, many proteins that are isolated from mammalian cells are gycosylated, thereby providing an additional target group that can be used for attachment. A notable example of such proteins are antibodies. Oxidation of IgG can be carried out in the dark at 4° C. for 20 minutes with 10 mM periodate at pH 4-5 to introduce aldehyde groups into the antibody. The excess periodate is removed afterwards by G50 fractionation. A modification reagent is prepared by reacting cystathione with Elman's Reagent thus blocking the thiol moiety with a removable group. The aldehyde groups on the glycon portion of the antibody are then reacted with a 40 fold excess of the modification reagent at pH 6 for one hour at room temperature. The pH is then raised to pH 9, the solution is cooled and the Schiff's base is reduced with NaBH$_4$. This reduces the Schiff's base to an amine and liberates the thiol. The excess NaBH$_4$ is destroyed by adding acetate buffer (pH 4). The thiol labeled IgG is now available for linkage with the either the maleimide derivatized reagent from Example 1 or the bromoacetyl modified reagent from Example 4. It should be noted that this method results in a very controlled extent of labeling since it only takes place on sites where gycosylation has taken place. For example, the antibody used in this example is glycosylated in the constant region. As such, attachment of the labeling reagent should not interfere with the variable region, the part of the antibody that is responsible for the binding of the antibody to its antigen target.

Example 6. Multisignal Reagent with a Reactive Group at the 3' End

A 29-mer oligonucleotide with the following structure is synthesized;

(SEQ ID NO: 2)
5'-U$^F$ T T T T T T U$^F$ T T T T T T U$^F$ T T T T T T U$^F$
T T T T T T U$^F$-NH$_2$-3' where the oligonucleotide comprises a 3' primary amine and uridines that have fluorescein labels (symbolized by U$^F$). Phosphoramidites and CPG for making an oligonucleotide with these modification are commercially available. Alternatively, a phosphoramidite for synthesis of an oligonucleotide with a primary amine in the 5' end could have been used to synthesize a similar labeled oligonucleotide. This product comprises 5 fluorescein moieties and a single amine group. This reagent may be used with the same processes described previously for Examples 1, 2, 3, 4 and 5.

Example 7. Use of Terminal Transferase to Synthesize a Multisignal Labeling Reagent a) A 27-mer oligonucleotide with the following structure is synthesized;

SEQ ID NO: 3
5'-U* T T T T T U* T T T T T U* T T T T T U*
T T T T T U*T T-3' where the oligonucleotide comprises allylamine modified uridines (symbolized by U*). Attachment of the active ester of Alexa Fluor 555 (Molecular Probes, Inc, Eugene, Oreg.) can be carried out by the methods previously described in Example 1.

b) The labeled oligonucleotide can be further reacted by the addition of a dideoxy version of allylamine dUTP by terminal transferase. This step will introduce a single amine group into the 3' end of the oligonucleotide, thereby creating a labeling regent with 5 Alexa dyes and a single amine group. This labeling reagent can then be used as described previously.

Example 8. Synthesis of Multisignal Labeling Reagent Using Mercuration

A 57-mer oligonucleotide with the following structure is synthesized:

SEQ ID NO: 4
5' (U T T T T T T)$_8$ T-NH$_2$-3' where the 3' end has an amine group. The oligonucleotide is treated with a 3 fold molar access of mercuric acetate in acetate buffer (ph 4.0) for 5 hours at 65° C. to mercurate the 5 position of the uridine ring of the oligonucleotides. The mercurated oligonucleotides are then precipitated with ethanol and kept at −20° C. until needed. The oligonucleotide is then reacted with a Cy dye that comprises a terminal double bond reactive group as described in U.S. Pat. No. 7,166,478. The resultant oligonucleotide should then comprise a single amine reactive group at the 3' end and a Cy dye at each of the 8 sites where there was a U. This labeling reagent may then be used as described above.

Example 9. Protein Labeled by Means of Two Strands of Nucleic Acid a) A 12-mer oligonucleotide with the following structure is synthesized;

(SEQ ID NO: 5)
5'-GTG U* GTG U* GTG U*-3' where the oligonucleotide comprises allylamine modified uridines (symbolized by U*).

b) The active ester of the TAMRA, rhodamine 110, or aphenylic Texas Red analogue used in Example 1 can be reacted with the allylamine moieties in the oligonucleotide to produce a Signal Oligonucleotide using the same procedures described above.

c) A 50-mer Attachment Oligonucleotide with the following structure is synthesized;

(SEQ ID NO: 6)
5'-(A C)$_{25}$-NH$_2$-3' d) The TAMRA, rhodamine 110, or Texas Red labeled signal oligonucleotide is annealed to the attachment oligonucleotide to form a multisignal labeling reagent. Due to the redundancy of the dinucleotide repeats, hybridization should enjoy fast kinetics. The signal oligonucleotides are smaller than the attachment oligonucleotide such that there is sufficient room for as many as 4 dignal oligonucleotides to bind to each attachment oligonucleotide of the multisignal labeling reagent. This would result in 12 signal moieties potentially being attached to every site on a target that is linked through the amine group of the multisignal labeling reagent. Using the 2° C. per A/T base-pair and 4° C. per G/C base-pair rule, the theoretical $T_m$ of the signal oligonucleotides should be about 36° C. As such, the multisignal labeling reagent complexes should be quite stable at room temperature. Even higher $T_m$s will probably be realized since hybridization of two signal oligonucleotides on adjacent sites of the attachment oligonucleotide should allow stacking interactions that will favor the thermal stability of each oligonucleotide.

e) The multisignal labeling reagent can be attached to a protein through the amine group as described previously to form a labeled protein comprising multiple signals at each attachment site on the protein.

Example 10. Preparation of Samples for a Protein Array a) A 15-mer oligonucleotide with the following structure is synthesized;

(SEQ ID NO: 7)
5'-TGCU* GCTG CU GC U*GC-3'
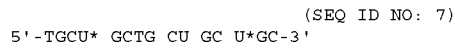

where the oligonucleotide comprises allylamine modified uridines (symbolized by U*)

b) The active ester of the TAMRA, rhodamine 110, or aphenylic Texas Red analogue is reacted with the allylamine moieties in the oligonucleotide to produce Signal Oligonucleotide #1 by the methods described previously in Example 1. The $T_m$ of this oligonucleotide should be about 50° C.

c) Attachment Oligonucleotide #1 (a 63-mer) with the following structure is synthesized;

(SEQ ID NO: 8)
5'-(GCA)$_{21}$ - NH$_2$ -3'
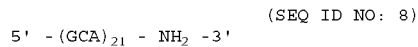

d) Signal Oligonucleotide #1 is annealed to Attachment Oligonucleotide #2 to form Multisignal Labeling Reagent #1 which at saturation values should have 8 TAMRA, rhodamine 110, or Texas Red moieties bound per 3' NH$_2$ group.

e) A 15-mer oligonucleotide with the following structure is synthesized;

(SEQ ID NO: 9)
5' - TCGU* CGTCGUCG U*CG- 3'

where the oligonucleotide comprises allylamine modified uridines (symbolized by U*).

f) Using the same methods as in step (b), the active ester of Alexa Fluor 647 (Molecular Probes, Inc, Eugene, Oreg.) is reacted with the allylamine moieties in the oligonucleotide to produce Multisignal Oligonucleotide #2. The $T_m$ of this oligonucleotide should also be about 50° C.

g) Attachment Oligonucleotide #2 (a 63-mer) with the following structure is synthesized;

(SEQ ID NO: 10)
5'-(CGA)$_{21}$ - NH$_2$ -3'
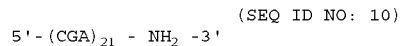

h) Signal Oligonucleotide #2 is annealed to Attachment Oligonucleotide #2 to form Multisignal Labeling Reagent #2 which at saturation values should have 8 Alexa moieties bound per 3' NH$_2$ group.

i) Protein sample #1 is reacted with Multisignal Labeling Reagent #1 from step (d) and Protein sample #2 is reacted with Multisignal Labeling Reagent #2 from step (d) using any of the methods described in the previous examples.

These samples are now ready to be applied to a protein array where signals from protein sample #1 (TAMRA, rhodamine 110, or Texas Red) will be distinguishable from signals from Protein sample #2 (Alexa). As described above, linkage of a multisignal labeling reagent of this Example of the present invention should allow joining as many as 8× the amount of signal moieties as would result from using a single dye with an amino group.

Example 11. Multisignal Labeling Reagent with Single-Stranded Tails a) A 50-mer attachment oligonucleotide with the following structure is synthesized;

(SEQ ID NO: 6)
5' -(A C)$_{25}$ - NH$_2$ -3'
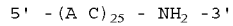

b) A 32-mer signal oligonucleotide with the following structure is synthesized;

(SEQ ID NO: 11)
5' - GTG U* GTG U* GTG U* G TG U* T T T U* T T T
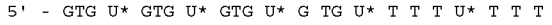
U* T T T U* T T T U* - 3'
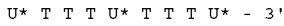

where the oligonucleotide comprises allylamine modified uridines (symbolized by U*)

c) The active ester of the TAMRA, rhodamine 110, or aphenylic Texas Red analogue is reacted with the allylamine moieties in the oligonucleotide to produce a tailed signal oligonucleotide. The 16 base segment at the 5' end of the signal oligonucleotide is complementary to the attachment oligonucleotide of step (a) and should have a $T_m$ of about 48° C. based on 8 G's and 8 T/U's. The 16 base 3' tail segment of the signal oligonucleotide consisting of T's and U*'s should contribute signal but should not participate in binding to the attachment oligonucleotide.

d) Hybridization of the signal oligonucleotides to the attachment oligonucleotide forms a multisignal labeling reagent that could provide as many as three signal oligonucleotides, each having 8 signal moieties, for a net total of 24 signal moieties potentially bound to each site where the attachment oligonucleotide portion of the multisignal labeling reagent will be linked to the protein target.

The unlabeled attachment oligonucleotide portion of the multisignal reagent is used for linkage to a protein through the amine group as described previously to form a labeled target comprising one or more multisignal labeling reagents.

Example 12. Double-Stranded Multisignal Labeling Reagent with Biotin as a Binding Partner a) A 50-mer biotinylated attachment oligonucleotide with the following structure is synthesized;

(SEQ ID NO: 6)
5'-(A C)$_{25}$ - biotin dU-3'
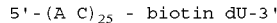

Phosphoramidites for a 3' biotin labeled nucleotide are readily available from numerous commercial sources.

b) The tailed signal oligonucleotides from step (c) of Example 9 are hybridized to the biotinylated attachment oligonucleotide to form a biotinylated multisignal labeling reagent. As described previously, this complex could comprise as many as 24 signal moieties with only a single biotin attachment moiety.

c) Biotinylated antibodies are readily available from a number of commercial sources. A biotinylated antibody can be can be bound to appropriate target antigens in a tissue section specimen and amplified detection of the presence of antigens can be carried out by first binding streptavidin followed by signal generation through binding of the Biotinylated Multisignal Labeling Reagent from step (b).

Example 13. Single-Stranded Multisignal Reagent with Biotin as a Binding Partner and Addition of Noise Suppressor a) a 61-mer oligonucleotide with the following structure is synthesized:

(SEQ ID NO: 12)
5'-Biotin U-(U* G T G T G T G T G)5-3' where the 5' end has a biotinylated U and the oligonucleotide comprises allylamine modified uridine moieties (symbolized as U*)

b) The active ester of Cy 3 dye (Amersham Biosciences, Piscataway, N.J.) can be reacted with the allylamine moieties in the oligonucleotide using the same procedures described above. To form a Cy3 labeled biotinylated multisignal labeling reagent:

c) a 20-mer oligonucleotide with the following sequence is synthesized:

(SEQ ID NO: 13)
5'- (TG)10-3' without labels or biotin to provide a noise suppressor.

d) PolyA mRNA is amplified according to the procedure described in US Patent Publication 2004/0161741, describing biotin incorporation during in vitro transcription of the double-stranded cDNA collection to produce labeled antisense RNA.

e) The biotinylated RNA is fragmented and hybridized to a High Density microarray chip form Affymetrix according to the manufacturer's instructions (Affymetrix, Inc. Santa Clara, Calif.).

e) The chips are incubated with strepavidin according to the Affymetrix instructions.

f) Instead of using biotinylated phycoerythrin as described in the Affymetrix instructions, the chip is incubated with a mixture of the Cy3 labeled biotinylated multisignal labeling reagent from step (b) and the noise suppressor from step (c).

g) After appropriate washing, signal generation from each locus is then measured.

Example 14. Single-Stranded Multisignal Labeling Reagent with Biotin as a Binding Partner and Addition of Unlabeled Complement a) a 61-mer oligonucleotide with the following structure is synthesized:

(SEQ ID NO. 12)
5'-Biotin U-(U* G T G T G T G T G)5-3' where the 5' end has a biotinylated U and the oligonucleotide comprises allylamine modified uridine moieties (symbolized as U*).

b) The active ester of Cy 3 dye (Amersham Biosciences, Piscataway, N.J.) can be reacted with the allylamine moieties in the oligonucleotide using the same procedures described above. To form a Cy3 labeled biotinylated multisignal labeling reagent.

c) A 20-mer oligonucleotide with the following structure is synthesized:

(SEQ ID NO: 14)
5'- (AC)10-3' without labels or biotin to provide a multisignal labeling reagent complement. The $T_m$ of this oligonucleotide should be about 60° C. based on 10 C's and 10 A's.

d) Poly A mRNA is amplified according to the procedure described in U.S. Pat. No. 7,166,478, where biotin is incorporated during in vitro transcription of the double-stranded cDNA collection to produce labeled anti-sense RNA.

e) The biotinylated RNA is fragmented and hybridized to a high density microarray chip from Affymetrix according to the manufacturer's instructions (Affymetrix, Inc., Santa Clara, Calif.).

e) The chips are incubated with strepavidin according to the Affymetrix instructions.

f) Instead of using biotinylated phycoerythrin as described in the Affymetrix instructions, the chip is incubated with a mixture of the Cy3 labeled biotinylated multisignal labeling reagent from step (b) and the multisignal reagent complement from step (c). Hybridization of the multisignal reagent complement to the Cy3 labeled biotinylated multisignal labeling reagent can take place during this step or if desired they can be preincubated together prior to application to the chip. By endowing the Cy3 labeled biotinylated multisignal labeling reagent with double-stranded character, quenching caused by interactions of the Cy 3 moieties could be reduced. Also if desired, the noise suppressor from step (c) of Example 11 may be included.

g) After appropriate washing, signal generation from each locus is then measured.

Example 15. Multisignal Labeling Reagent with Biotin and Energy Transfer a) a 61-mer oligonucleotide with the following structure is synthesized:

(SEQ ID NO: 15)
5'-Biotin U- (C$^F$ A C A C A C A C A)5-3' where the 5' end has a biotinylated U and the oligonucleotide comprises fluorescein modified cytidine moieties (symbolized as C$^F$) to form an energy donor multisignal labeling reagent.

b) a 20-mer oligonucleotide with the following structure is synthesized:

(SEQ ID NO: 16)
5'-T G T G U* G T G T G T G U* G T G T G-3' where the 5' end has a biotinylated U and the oligonucleotide comprises allylamine modified uridine moieties (symbolized as U*). The $T_m$ of this oligonucleotide should be about 60° C. based on 10 G's and 10 T/U's.

c) The active ester of TAMRA, rhodamine 110, or aphenylic Texas Red can be reacted with the allylamine moieties in the oligonucleotide using the same procedures described above to form an energy acceptor multisignal labeling reagent.

d) The energy donor multisignal labeling reagent from step (a) and the energy acceptor multisignal labeling reagent from step (c) are hybridized together to form an energy transfer multisignal labeling reagent which comprises a single biotin and as many as 5 donors and 6 acceptors.

e) The energy transfer multisignal labeling reagent can then be used as described above.

Example 16. Synthesis of Streptavidin-Oligonucleotide Bioconjugates

Protocol for Making Streptavidin-Oligo-22Mer Bioconjugates a) Preparation of Formylbenzoic Acid-Tagged Oligonucleotide (FB-Oligonucleotide)

To a solution of 5'-amino-oligo22mer having the sequence [amino-C6]TTGCTGAGGT CATGGATCGA GA (SEQ ID NO:17) (Eurofins, 30 nmole), in a buffer containing 100 mM phosphate and 150 mM NaCl, pH 7.4, 600 nmole of 4-formylbenzoic acid NETS-ester in DMF was added. The mixture was incubated at room temperature for 2 h and the labeled oligonucleotide, FB-oligonucleotide, was desalted using a 5 k MWCO VivaSpin diafiltration apparatus. FB-oligonucleotide concentration was determined spectroscopically at 260 nm.

b) Preparation of HyNic-Tagged Streptavidin (HyNic-STV)

Streptavidin (Thermo) was desalted into the buffer described under a) above using a Zeba Spin Column. The acetonide of 2-hydrazinoisonicotinic acid NETS-ester (200 nmole) in DMF was then added to 20 nmole of the desalted streptavidin. The reaction mixture was incubated at room temperature for 1.5 h and the labeled protein, HyNic-STV, was desalted into the above buffer, pH 6.0 using a 30 k Amicon diafiltration device. HyNic-STV concentration was measured spectroscopically at 280 nm and the molecular substitution ratio (MSR) was determined with 2-sulfo-benzaldehyde reagent.

c) Conjugation of HyNic-STV with FB-Oligonucleotide-1:1 STV:Oligo Molar Ratio

Desalted HyNic-STV (16.7 nmole) described in b) above was mixed with FB-oligonucleotide (30 nmole) prepared as described in a) above in the above-described buffer, pH 6.0, along with 100 mM aniline as a catalyst. The reaction mixture was incubated at room temperature for 2 h and the bioconjugate was desalted using a 30 k Amicon diafiltration device. The STV-Oligonucleotide bioconjugate concentration was measured spectroscopically at 354 nm and the purity was determined by 4-16% native gel polyacrylamide electrophoresis followed by sequential staining with ethidium bromide and Coomassie stain.

d) Conjugation of HyNic-STV with FB-Oligonucleotide-1:2 STV:Oligo Molar Ratio

Desalted HyNic-STV (10 nmole) was mixed with FB-oligonucleotide (25 nmole) in the above-described buffer, pH 6.0, along with 100 mM aniline as a catalyst. The reaction mixture was incubated at room temperature for 2 h and the bioconjugate was desalted using a 30 k Amicon diafiltration device. STV-oligonucleotide bioconjugate concentration was measured spectroscopically at 354 nm and the purity was determined by 4-16% native gel polyacrylamide electrophoresis followed by sequential staining with ethidium bromide and Coomassie stain.

Protocol for Making Streptavidin-Oligo-60Mer Bioconjugate a) Preparation of Formylbenzoic Acid-Tagged Oligonucleotide (FB-Oligonucleotide)

To a solution of 5-amino-oligo60mer having the sequence [amino-C6]TTTTGACACG GGTCCTATGC CTTGACACGG GTCCTATGCC TTGACACGGG TCCTATGCCT (SEQ ID NO:18) (Eurofins, 10 nmole) in the above-described buffer, pH 7.4, 200 nmole of 4-formylbenzoic acid NETS-ester in DMF was added. The mixture was incubated at room temperature for 2 h and the labeled oligonucleotide, FB-oligonucleotide, was desalted using a 5 k MWCO VivaSpin diafiltration apparatus. FB-oligonucleotide concentration was determined spectroscopically at 260 nm.

b) Preparation of NyNic-Tagged Streptavidin (HyNic-STV)

Streptavidin (Thermo) was desalted into the buffer described above using Zeba Spin Column. To 10 nmole of this desalted streptavidin in the above buffer, 100 nmole of the acetonide of 2-hydrazinoisonicotinic acid NETS-ester in DMF was added. The reaction mixture was incubated at room temperature for 1.5 h and the labeled protein, HyNic-STV, was desalted into the above-described buffer, pH 6.0 using a 30 k Amicon diafiltration device. HyNic-STV concentration was measured spectroscopically at 280 nm while the molecular substitution ratio (MSR) was determined with 2-sulfo-benzaldehyde reagent.

c) Conjugation of HyNic-STV with FB-Oligonucleotide

Desalted HyNic-STV (6 nmole) described in b) above was mixed with FB-oligonucleotide (10 nmole) prepared as described in a) above in the above-described buffer, pH 6.0, along with 100 mM aniline as a catalyst. The reaction mixture was incubated at room temperature for 2 h and the bioconjugate was desalted using 30 k Amicon diafiltration device. The STV-oligonucleotide bioconjugate concentration was measured spectroscopically at 354 nm and the purity was determined by 4-16% Native gel polyacrylamide electrophoresis followed by sequential staining with SYBR Gold and Coomassie stain.

Example 17. Synthesis of Alkaline Phosphatase-Oligo-20Mer Bioconjugates

Note: Two oligo-20mers, one containing biotin (control) and one without biotin (probe), were prepared in parallel. Otherwise the sequences of both oligomers were identical.

a) Preparation of Labeled Oligonucleotides (FB-Oligonucleotide)

20NoBiotinAminoC6—Alkaline Phosphatase-Oligonucleotide Bioconjugate (the probe):

(SEQ ID NO: 19)
[AminoC6]TTTTAGCTTTTCAGTTTTGACTA

20BiotinAminoC6—the control for Alkaline Phosphatase-Oligonucleotide Bioconjugate:

(SEQ ID NO: 19)
[AminoC6]TTTTAGCTTTTCAGTTTTGACTA + biotin (on 3' end)

To 1 mM solution of 5'-amino-oligo20mers (Eurofins, 50 nmole) in a buffer containing 100 mM phosphate and 150 mM NaCl at pH 7.4, 20 molar equivalents (1.0 µmole) of 4-formylbenzoic acid NETS-ester (Solulink) in DMF was added. The mixture was incubated at room temperature for 2 h and the labeled oligonucleotides, FB-oligonucleotides, were desalted using 3k Amicon diafiltration devices (14,000×g, 20 min). FB-Oligonucleotide concentration was determined spectroscopically at 260 nm.

b) Preparation of Labeled Alkaline Phosphatase (HyNic-AP)

Alkaline phosphatase (Thermo) was desalted into the buffer described in a) above using Zeba Spin Column. Then, to 70 nmole of desalted protein in the above buffer, 20 molar equivalents (1.4 µmole) of the acetonide of 2-hydrazinoisonicotinic acid NETS-ester (Solulink) in DMF was added. The reaction mixture was incubated at room temperature for 1.5 h and the labeled protein, HyNic-AP, was desalted into the above-described buffer, pH 6.0 using a 30 k Amicon diafiltration device. HyNic-AP concentration was measured spectroscopically at 280 nm while the molecular substitution ratio (MSR) was determined with 2-sulfobenzaldehyde reagent (Solulink).

c) Conjugation of HyNic-AP with FB-oligonucleotides

Desalted HyNic-AP (28 nmole) described in b) above was mixed with each of the FB-oligonucleotides (50 nmole) prepared as described in b) above in the above-described buffer, pH 6.0, along with and 100 mM aniline as a catalyst. The reaction mixtures were incubated at room temperature for 2 h and the bioconjugates were desalted using 30 k Amicon diafiltration devices. AP-oligonucleotide bioconjugate concentration was measured spectroscopically at 354 nm and the purity was determined by 4-16% native gel polyacrylamide electrophoresis followed by sequential staining with ethidium bromide and Coomassie stain.

Example 18. Adding Multiple Labels to a Single Reporter Molecule Using DNA Polymerase A short oligonucleotide with the sequence 5'-C6 amino-TTGCTGAGGT CATGGATCGA GA-3' (SEQ ID NO:17) is attached to streptavidin as described in Example 16, using the protein oligo conjugation kit (Solulink, San Diego, Calif., catalog # S-9011-1). The streptavidin oligo conjugate is mixed with a template oligo of the sequence 5'-ACTTCTACTT CTACTTCTAC TTCTACTTCT ACTTCTACTT CTACTTCTAC TCTTACTCTT ACTCTTCATT GGT-CATCTCG ATCCATGACC TCAGC-3'. (SEQ ID NO:20) 172 pMol of the streptavidin oligo construct is incubated with 200 pMol of template oligo in 50 mM NaCl, 10 mM Tris-HCl, 10 mM MgCl$_2$, 1 mM dithiothreitol, pH 7.9, 5 nMol rhodamine-dUTP (fluorescein dUTP has also been used successfully), 15 nMol each dATP, dCTP and dGTP and 6 units of *E. coli* DNA polymerase I Klenow fragment exo$^-$ (New England Biolabs, Ipswich, Mass.) in a total volume of 20 µl at 37° C. for 2 hours. The extension reaction was stopped with 2 µl of 500 mM EDTA, and the unincorporated nucleotides are removed using NucAway spin columns (Applied Biosystems/Ambion, Austin, Tex.) as described by the manufacturer. FIG. 2 is a diagram of this procedure.

A model system for in situ hybridization is HPV16/18 integration into the chromosome of different cell lines. HeLa cells have 30-50 copies of HPV18 integrated into its chromosome and SiHa cells have 1-5 chromosomal copies of HPV16 (Schwarz et al., 1995, Nature 314:111-114; Micheva et al., 1987, Med Microbiol Immunol 176:245-256). The cells HeLa, SiHa and the HPV negative control SK-N-SH (ATCC, Manassas, Va.) were grown on slides at a density of about 10$^5$ cells/ml. After growth overnight in Eagle's Minimum Essential Medium supplemented with 10% fetal bovine serum (FBS, ATCC) and 100 u/ml penicillin with 100 µg/ml streptomycin (Sigma-Aldrich, St. Louis, Mo.) at 37° C., 5% CO$_2$ in a humidified chamber, the cells were washed for 5 minutes in PBS, then fixed in 100% Acetone for 5 minutes, followed by air drying. The slides were treated in 10 mM sodium citrate at 80° C. for 1 hour, then washed in 2×SSC (Sambrook and Russell, 2001, Molecular Cloning: A Laboratory Manual. Cold Spring Harbor, N.Y., CSHL Press) for 5 minutes. DNA was denatured at 73° C. for 5 minutes in 70% formamide, 2×SSC, followed by 70% ethanol for 1 minute, 90% ethanol 1 minute and 100% ethanol for 1 minute followed by drying at 37° C. for 2 minutes. 12 µl of HPV16/18 biotinylated DNA probe (ENZO Life Sciences, Farmingdale, N.Y.) was added to each well of cells, and then a coverslip was added and sealed with rubber cement. The probe was denatured at 80° C. for 5 minutes, and then hybridization was performed overnight at 37° C. in a humidified chamber. The following day, the coverslip was removed and the slide was washed in PBS for 5 minutes, then in 40% formamide, 6×SSPE (Id.) at 37° C. for 10 minutes. The slide was again washed with PBS, then with Superblock in TBS (Thermo Scientific, Rockford, Ill.) for 15 minutes. Detection was achieved by incubation of 30 nM labeled streptavidin in Superblock in TBS containing 200 µg/ml single-stranded salmon sperm DNA (80 µl per well) at room temperature in the dark for 1 hour. This was washed with PBS for 1 minute, and then incubated with PBS containing 0.5 Hoechst 33342 for 15 minutes at room temperature for a nuclear counter stain. Two washes in PBS removed excess dye. The wells were kept moist with PBS, and a coverslip was added for visualization. Cells were observed using a fluorescence microscope (Carl Zeiss MicroImaging GmbH, Jena, Germany) equipped with a Texas Red filter set for rhodamine, a DAPI filter set for Hoechst and a FITC filter set for fluorescein. Images were acquired with a 63× objective lens (Carl Zeiss, Inc).

FIG. 3 shows that streptavidin with the extended oligos (13 rhodamines) can detect 1 to 5 copies of HPV16 in SiHa cells with very little background in control cells (SK-N-SH) lacking HPV16. In these conditions plain rhodamine, streptavidin or phycoerythrin streptavidin (Life Technologies, Eugene, Oreg.) failed to detect the HPV16 in SiHa cells (data not shown). The inability of phycoerythrin streptavidin to detect the HPV may be due to the large size of the fluorescent molecule preventing access to the biotinylated probe DNA.

Example 19 Combining Extended Oligo with Branched DNA

A multiple rhodamine labeled oligo was created by mixing the following oligos:

Mext6-
(SEQ ID NO: 21)
5'-TACTGCTACTGCTACTTCTACTGCTACTGCTACTTCTACTGCTACTC

TGACTCTGACTCTTCATTGGTCACTACACCAACAGCATGAC-3'

LPrimS-
(SEQ ID NO: 22 and SEQ ID NO: 23, respectively)
5'-AGGCATAGGACCCGTGTCTTT[spacer][spacer]GTCATGCTGT

TGGTGTAG-3'

Where "[spacer]" is a 9 atom chain that has no base and cannot be used as a template.

LPrimS (8 pmoles) was mixed with 8.8 pmoles Mext6 in the presence of 26 nmoles dATP, dCTP and dGTP, and 11.6 nmoles rhodamine-5-dUTP. DNA polymerase I Klenow exo$^-$ (5 units) in a buffer containing 50 mM sodium chloride, 20 mM tris acetate, 10 mM magnesium acetate, 1 mM dithiothreitol and 500 mM trehalose was added to the above mixture and incubated at 46° C. for 1 h. The labeled oligo was purified from unincorporated nucleotides using Nuc-Away spin columns (Applied Biosystems, Austin, Tex.) according to the manufacturer's instructions. The 5' end of LprimS remains single-stranded and free to bind a second oligonucleotide. Similar labeling of a single end of a primer could be achieved with the use of a 3' end blocked terminus of the template oligo.

The branched DNA was produced by mixing 262.5 pmoles of the extended oligo from above with 50 pmoles of Bio-Linker (5'-biotin-TATGACACGGGTCCTATGCCTT-GACACGGGTCCTATGCCTTGACACGGGTCCTATGC-CTTGACACGGGTCCTATGCCTTGACACGGGTC-CTATGCCT-3') (SEQ ID NO:24) that has 5 binding sites for the single-stranded portion of the extended oligo. This was mixed while stirring at a 1:1 ratio with streptavidin, starting with 5.9 µM streptavidin and 5.9 µM of the Bio-Linker branch in PBS. The resulting product should on average have one branched oligo per streptavidin, leaving two or three biotin binding sights on the streptavidin free.

The resulting complex was diluted to 10 nM or 5 nM in Superblock in TBS (Thermo Scientific, Rockford, Ill.). The extended oligo rhodamine-labeled streptavidin from Example 18 was diluted in a similar manner to 10 nM and 5 nM. 100 µl of the labeled streptavidin solutions were used to bind pre-blocked biotin-coated 96 well plates (G-Biosciences, Maryland Heights, Mo.) in duplicate. The streptavidin was allowed to bind for one hour at room temperature with slow shaking (100 RPM). After binding, the wells were washed 4 times with PBS containing 0.05% Tween 20. 60 µl PBS was added to each well of the plate, and the plate was read from the top using a BioTek SynergyMX (Winooski, Vt.) at 554 nm excitation and 584 emission using a 9 nm slit width for each. The results were as follows:

|  | Oligo-streptavidin | Bio-linker/LPrimS mix |
| --- | --- | --- |
| 10 nM | 972 | 3,440 |
| 5 nM | 579 | 2,169 |
| 0 nM | 24 | 21 |
| 10 nM pre-blocked with 20 µM streptavidin | 25 | 63 |

The binding of the 10 nM streptavidin complexes was eliminated if 20 µM streptavidin was first bound to the plate before the labeled streptavidin was added. It can be seen that the signal of the branched reagent is increased about four fold over the linear reagent. This demonstrates that the extended, branched oligo is functional and specific.

Example 20. Synthesis of Spermidine-Diacridine (Compound 1)

Heat a mixture of phenol (3.51 g, 37.3 mmol) and 9-chloroacridine (1.6 g, 7.46 mmol) in an oil bath at 120° C. for 1 h. To this mixture add spermidine (0.54 g, 0.58 mL, 3.73 mmol) and continue heating for another 2.5 h. Pour into 75 mL of 2 N NaOH solution and extract with chloroform (2×50 mL). Wash the organic layer with 1N NaOH (1×75 mL), water (2×100 mL), brine (2×100 mL) and dry with MgSO₄. Recrystallize the yellow solid thus obtained with ethanol to obtain Compound 1 (30% yield). The structure of Compound 1 is given below:

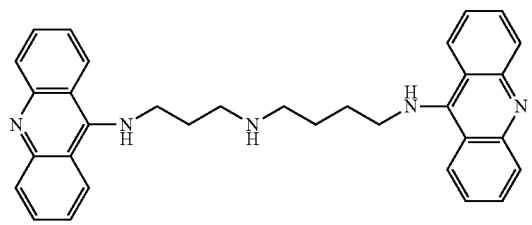 [SMILES: c1ccc2c(NCCCCNCCCNc3c4ccccc4nc4ccccc34)c3ccccc3nc2c1]

Example 21. Synthesis of Spermidine-6-chloro-2-methoxydiacridine (Compound 2)

The procedure can be carried out as described in Example 20 using 6-chloro-2-methoxy acridine, phenol and spermidine. The structure of Compound 2 is given below:

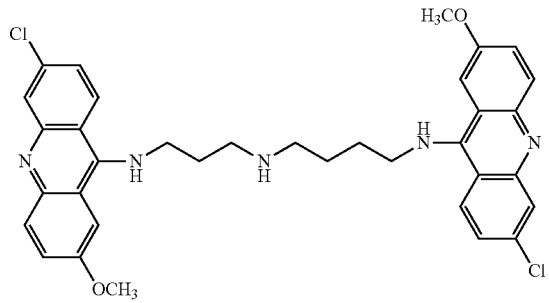 [SMILES: COc1ccc2nc3cc(Cl)ccc3c(NCCCCNCCCNc3c4ccc(Cl)cc4nc4ccc(OC)cc34)c2c1]

Example 22. General Procedure for Labeling Dyes to Diacridine Derivatives

Cool (in an ice bath) a solution of dye acid (1 eq.) and diisopropylethyl amine (3 eq.) in DMF under stirring. Add Bromo-tris-pyrrolidino phosphoniumhexafluorophosphate (PyBrop) (1 eq.) and continue stirring in the ice bath for 15 minutes. Add the appropriate diacridine derivative from Example 20 or 21 and continue stirring in the ice bath for another 15 minutes and at room temperature for 12 hours. Add a mixture of dichloromethane and water (1:1) to the reaction. Wash the organic layer with water and brine and dry over MgSO₄. Evaporate the solvent and obtain the desired product by purification on Biotage using a SNAP column. General structure of the conjugate is shown below:

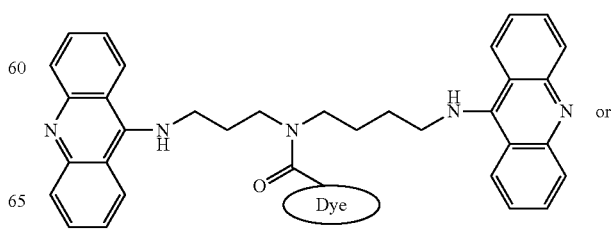

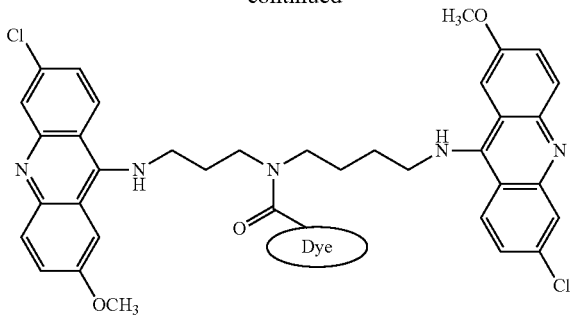

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of producing a multisignal labeling reagent, the method comprising
   (a) obtaining
      (i) a primer comprising an oligonucleotide and a first reactive group or a first partner of a first binding pair at the 5' end of the oligonucleotide;
      (ii) a template comprising a nucleic acid comprising a first sequence that is complementary to the oligonucleotide and a second sequence that extends in the 5' direction from the first sequence;
      (iii) a polymerase capable of extending the oligonucleotide along the template nucleic acid when the template nucleic acid is hybridized to the oligonucleotide at the first sequence; and
      (iv) nucleotide triphosphates (NTPs) or analogs thereof that are capable of being incorporated into the extended oligonucleotide, wherein at least one of the NTPs or analogs comprises a non-radioactive detectable label, a second reactive group or a first partner of a second binding pair; and
   (b) combining the primer, template, polymerase and NTPs or analogs under conditions such that the oligonucleotide hybridizes to the first sequence and is extended along the second sequence, where the extended oligonucleotide comprises at least two NTPs or analogs incorporated therein that comprise a non-radioactive detectable label, a second reactive group or a first partner of a second binding pair;
   wherein,
      (A) if at least one of the at least two NTPs or analogs incorporated into the extended oligonucleotide comprises a second reactive group, the method further comprises combining the extended oligonucleotide with a first compound comprising a non-radioactive detectable label covalently linked to a moiety capable of reacting with the second reactive group such that the label is covalently linked to the extended primer, and
      (B) if at least one of the at least two NTPs or analogs incorporated into the extended oligonucleotide comprises a first partner of the second binding pair, the method further comprises combining the extended primer with a second compound comprising the non-radioactive detectable label covalently linked to a second binding partner of the second binding pair.

2. The method of claim 1, wherein the non-radioactive detectable labels are fluorophores, phosphorescent moieties, chemiluminescent moieties, chelating moieties, electron dense moieties, magnetic moieties, or energy transfer moieties.

3. The method of claim 1, wherein the non-radioactive detectable labels are fluorophores.

4. The method of claim 3, wherein the fluorophore comprises a symmetric or asymmetric cyanine, a merocyanine, a styryl moiety, an oxazine, a xanthene, a coumarin or an iminocoumarin.

5. The method of claim 1, wherein the fluorophore comprises a xanthene.

6. The method of claim 5, wherein the xanthene is a rhodamine or rhodamine derivative.

7. The method of claim 5, wherein the xanthene is a rosamine or rosamine derivative.

8. The method of claim 5, wherein the xanthene is a rhodol or rhodol derivative.

9. The method of claim 3, wherein the fluorophore comprises a coumarin.

10. The method of claim 3, wherein the coumarin is an iminocoumarin.

11. The method of claim 1, wherein the non-radioactive detectable labels are chemiluminescent or phosphorescent moieties.

12. The method of claim 11, wherein the NTP or NTP analogs are each labeled with a non-radioactive detectable label.

13. The method of claim 1, wherein the at least two NTPs or analogs incorporated into the extended oligonucleotide are each labeled with a reactive group.

14. The method of claim 13, wherein each reactive group is joined to the NTPs by a linker arm.

15. The method of claim 13, wherein the reactive group is an isothiocyanate, isocyanate, monochlorotriazine, dichlorotriazine, mono- or di-halogen substituted pyridine, mono- or di-halogen substituted diazine, maleimide, aziridine, sulfonyl halogen substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal, aldehyde, mercury salt, or any combination thereof.

16. The method of claim 1, wherein the NTP or NTP analogs are each labeled with a first binding partner of a second binding pair.

17. The method of claim 16, wherein the first binding partner of the second binding pair is a biotin.

18. The method of claim 15, wherein each first binding partner of the second binding pair is connected to the NTPs by a linker arm.

19. The method of claim 1, wherein the multisignal labeling reagent further comprises a non-inherent charged group that increases the aqueous solubility of the reagent.

20. The method of claim 19, wherein the charged group is a phosphate, a carboxylic acid, a sulfone, an amine or a hydroxy group.

21. The method of claim 1, wherein the primer comprises a first partner of a first binding pair.

22. The method of claim 21, wherein the first binding pair is a ligand/receptor, a hormone/receptor, biotin/avidin, biotin/streptavidin or an antigen/antibody.

23. The method of claim 21, wherein the first partner of the first binding pair is streptavidin.

24. The method of claim 1, further comprising combining the multisignal labeling reagent with a target molecule such that the multisignal labeling reagent is bound to the target by the first reactive group or the first partner of the first binding pair.

* * * * *